(12) United States Patent
Sytkowski et al.

(10) Patent No.: US 6,287,777 B1
(45) Date of Patent: Sep. 11, 2001

(54) NPG-1 GENE THAT IS DIFFERENTIALLY EXPRESSED IN PROSTATE TUMORS

(75) Inventors: Arthur J. Sytkowski, Arlington; Meiheng Yang, Norwood, both of MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/371,696

(22) Filed: Aug. 10, 1999

Related U.S. Application Data

(63) Continuation-in-part of application No. 09/022,238, filed on Feb. 11, 1998, which is a continuation-in-part of application No. 08/644,326, filed on May 10, 1996, now Pat. No. 5,804,382.

(51) Int. Cl.$^7$ .............................. C12Q 1/68; C12P 19/34
(52) U.S. Cl. ................................................ 435/6; 435/91.2
(58) Field of Search ............................. 435/6, 91.1, 91.2

(56) References Cited

PUBLICATIONS

Ashar et al., "Genomic Characterization of Human HMGIC, a Member of the Accessory Transcription Factor Family Found at Translocation Breakpoints in Lipomas" Genomics 31:207–214; 1996.
Byrne et al., "A Screening Method to Identify Genes Commonly Overexpressed In Carcinomas And The Identification Of A Novel Complementary DNA Sequence" Cancer Research 55:2896–2903, 1995.
Castle et al., "Antisense–medicated Reduction in Thrombospondin Reverses the Malignant Phenotype of a Human Sqaumous Carcinoma" J. Clin. Invest. 87:1883–1888, 1991.
Chau et al., "The Gene for the Human Architectural Transcription Factor HMGI–C Consists of Five Exons Each Coding for a Distinct Functional Element" Nucleic Acids Research 23(21):4262–4266, 1995.
Chiquet–Ehrismann, "Tenascin and Other Adhesion–modulating Proteins in Cancer" Seminars in Cancer Biology 4:301–310, 1993.
Copy of GenBank® Search Using the NPG–1 Gene.
Copy of Genbank® Search Using the NPG–1 Protein.
GenBank® Accession Number AF025847 for Myxococcus xanthus (p)ppGpp synthetase (relA), and DfrA (dfrA) genes, complete cds..
GeneBank® Accession Number AA671880for v107d08.r2 Sores mouse mammary gland NbMMG Mus musculus cDNA clone 963471 5' similar to SW:FSPO_RAT P35446F–SPONDIN PRECURSOR.;, mRNA sequence.
GenBank® Accession Number AA047125 for zk79b09.r1 Soares pregnant uterus NbHPU Homo sapiens cDNA clone 489017 5', mRNA sequence.
Higashijimia et al., "Mindin/F–spondin Family: Novel ECM Proteins Expressed in the Zebrafish Embryonic Axis" Developmental Biology 192:211–227, 1997.
Hosokawa et al., "The Effect of Thrombospondin on Invasion of Fibrin Gels by Human A549 Lung Carcinoma" Oncology Research 5(4/5):183–189, 1993.
Jothy et al., "Adhesion or Anti–adhesion in cancer: What Matters More?", Cancer and Metastasis Reviews 14:363–376, 1995.
Khleborarova et al., "The Mink Proopiomelanocortin Gene: Characterization of cDNA and Chromosonal Localization" Genomics 2:185–188, 1988.
Klar et al., "F–Spondin: A Gene Expressed at High Levels in the Floor Plate Encodes a Secreted Protein that Promotes Neural Cell Adhesion and Neurite Extension" Cell 69:95–110, 1992.
Manfioletti et al., "cDNA Cloning of the HMGI–C Phosphoprotein, a Nuclear Protein Associated with Neoplastic and Undifferentiated Phenotypes" Nucleic Acids Research 19:6793–6797, 1991.
Patel et al., "Expression and cDNA Cloning of Human HMGI–C Phosphoprotein" Biochemical Biophysical Research Communications 201(1):63–70, 1994.
Price et al., "Biochemistry of Cancer Dissemination" Critical Reviews in Biochemistry and Molecular Biology 32(3):175–253, 1997.
Qian et al., "Expression of Thrombospondin–1 in Cancer: A Role in Tumor Progression" Proceedings of the Society for Experimental Biology and Medicine 212(3):199–207, 1996.
Shoenmakers et al., "Identification, Molecular Cloning, and Characterization of the Chromosome 12 Breakpoint Cluster Region of Uterine Leiomyomas" Genes, Chromosomes & Cancer 11:106–118, 1994.
Shen et al., "Identification of the Human Prostatic Carcinoma Oncogene PTI–1 By Rapid Expression Cloning and Differential RNA Display", Proceedings National Academy of Science 92:6778–6782, 1995.
Taraboletti et al., "Thrombospondin–induced Tumor Cell Migration: Haptotaxis and Chemotaxis Are Mediated by Different Molecular Domains" J. Cell Biology, 105:2409–2415, 1987.
Tuszynski et al., "The Role of Thrombospondin–1 in Tumor Progression and Angiogenisis" BioEssays 18:(1):71–76, 1996.
Tuszynski et al., "Thrombospondin Promotes Cell–Substratum Adhesion" Science 236:1570–1573, 1987.
Wang et al., "Two Differentialy Expressed Genes in Normal Human Prostate Tissue and In Carcinoma" Cancer Research 56:3634–3637, 1996.

*Primary Examiner*—Eggerton A. Campbell
(74) *Attorney, Agent, or Firm*—Fish & Richardson P.C.

(57) ABSTRACT

The invention provides isolated nucleic acids molecules, designated NPG-1 nucleic acid molecules, which encode polypeptides involved in the modulation of a response in a tumor cell. The invention also provides antisense nucleic acid molecules, expression vectors containing NPG-1 nucleic acid molecules, host cells into which the expression vectors have been introduced, and non-human transgenic animals in which an NPG-1 gene has been introduced or disrupted. The invention still further provides isolated NPG-1 polypeptides, fusion polypeptides, antigenic peptides, and anti-NPG-1 antibodies. Diagnostic, screening, and therapeutic methods utilizing compositions of the invention are also provided.

14 Claims, 3 Drawing Sheets

```
tgggcagggc gagttgggaa agcggcagcc ccgccgccc ccgcagcccc ttctcctctt    60
tctcccacgt cctatctgcc tctcgctgga ggccaggccg tgcagcatcg aagacaggag  120
gaactggagc ctcattggcc ggcccggggc gccggcctcg ggcttaaata ggagctccgg  180
gctctggctg ggacccgacc gctgccggcc gcgctcccgc tgctcctgcc gggtg atg   238
                                                             Met
                                                             1
```

| | | | | | | | | | | | | | | | | |
|---|---|---|---|---|---|---|---|---|---|---|---|---|---|---|---|---|
| gaa | aac | ccc | agc | ccg | gcc | gcc | gcc | ctg | ggc | aag | gcc | ctc | tgc | gct | ctc | 286 |
| Glu | Asn | Pro | Ser | Pro | Ala | Ala | Ala | Leu | Gly | Lys | Ala | Leu | Cys | Ala | Leu | |
| | | 5 | | | | | 10 | | | | | 15 | | | | |

```
ctc ctg gcc act ctc ggc gcc gcc ggc cag cct ctt ggg gga gag tcc    334
Leu Leu Ala Thr Leu Gly Ala Ala Gly Gln Pro Leu Gly Gly Glu Ser
        20              25              30 atc tgt tcc gcc aga gcc ccg gcc aaa tac agc atc acc ttc acg ggc    382
Ile Cys Ser Ala Arg Ala Pro Ala Lys Tyr Ser Ile Thr Phe Thr Gly
    35              40              45 aag tgg agc cag acg gcc ttc ccc aag cag tac ccc ctg ttc cgc ccc    430
Lys Trp Ser Gln Thr Ala Phe Pro Lys Gln Tyr Pro Leu Phe Arg Pro
50              55              60              65 cct gcg cag tgg tct tcg ctg ctg ggg gcc gcg cat agc tcc gac tac    478
Pro Ala Gln Trp Ser Ser Leu Leu Gly Ala Ala His Ser Ser Asp Tyr
            70              75              80 agc atg tgg agg aag aac cag tac gtc agt aac ggg ctg cgc gac ttt    526
Ser Met Trp Arg Lys Asn Gln Tyr Val Ser Asn Gly Leu Arg Asp Phe
            85              90              95 gcg gag cgc ggc gag gcc tgg gcg ctg atg aag gag atc gag gcg gcg    574
Ala Glu Arg Gly Glu Ala Trp Ala Leu Met Lys Glu Ile Glu Ala Ala
        100             105             110 ggg gag gcg ctg cag agc gtg cac gag gtg ttt tcg gcg ccc gcc gtc    622
Gly Glu Ala Leu Gln Ser Val His Glu Val Phe Ser Ala Pro Ala Val
115             120             125 ccc agc ggc acc ggg cag acg tcg gcg gag ctg gag gtg cag cgc aag    670
Pro Ser Gly Thr Gly Gln Thr Ser Ala Glu Leu Glu Val Gln Arg Lys
130             135             140             145 cac tcg ctg gtc tcg ttt gtg gtg cgc atc gtg ccc agc ccc gac tgg    718
His Ser Leu Val Ser Phe Val Val Arg Ile Val Pro Ser Pro Asp Trp
            150             155             160 ttc gtg ggc gtg gac agc ctg gac ctg tgc gac ggg gac cgt tgg cgg    766
Phe Val Gly Val Asp Ser Leu Asp Leu Cys Asp Gly Asp Arg Trp Arg
            165             170             175 gaa cag gcg gcg ctt gac ctg tac ccc tac gac gcc ggg acg gac agc    814
Glu Gln Ala Ala Leu Asp Leu Tyr Pro Tyr Asp Ala Gly Thr Asp Ser
        180             185             190 ggc ttc acc ttc tcc tcc ccc aac ttc gcc acc atc ccg cag gac acg    862
Gly Phe Thr Phe Ser Ser Pro Asn Phe Ala Thr Ile Pro Gln Asp Thr
195             200             205 gtg acc gag ata acg tcc tcc tct ccc agc cac ccg gcc agc tcc ttc    910
Val Thr Glu Ile Thr Ser Ser Ser Pro Ser His Pro Ala Ser Ser Phe
```

FIG. 2A

|  |  |  |  |  |  |  |  |  |  |  |  |  |  |  |
|---|---|---|---|---|---|---|---|---|---|---|---|---|---|---|
| 210 | | | | 215 | | | | 220 | | | | 225 | | |

```
    tac tac ccg cgg ctg aag gcc tgc tcc cat cgc cag ggt gac act ggt      958
    Tyr Tyr Pro Arg Leu Lys Ala Cys Ser His Arg Gln Gly Asp Thr Gly
                    230                 235                 240 gcg gct gcg aca gag ccc cag ggc ctt cat ccc tcc cgc ccc agt cct     1006
    Ala Ala Ala Thr Glu Pro Gln Gly Leu His Pro Ser Arg Pro Ser Pro
                    245                 250                 255 gcc cag cag gac aat gcg ctt gta gac agc gcc tca gtt cca gaa aca     1054
    Ala Gln Gln Asp Asn Ala Leu Val Asp Ser Ala Ser Val Pro Glu Thr
                    260                 265                 270 ccg ctg gac tgc gag gtc tcc ctg tgg tcg tcc tgg gga ctg tgc gga     1102
    Pro Leu Asp Cys Glu Val Ser Leu Trp Ser Ser Trp Gly Leu Cys Gly
                    275                 280                 285 ggc cac tgt ggg agg ctc ggg tcc aag agc agg act ccg tac gcc cgg     1150
    Gly His Cys Gly Arg Leu Gly Ser Lys Ser Arg Thr Pro Tyr Ala Arg
    290                 295                 300                 305 gtc cag ccc gcc aac aac ggg agc ccc tgc ccc gag ctc gaa gaa gag     1198
    Val Gln Pro Ala Asn Asn Gly Ser Pro Cys Pro Glu Leu Glu Glu Glu
                    310                 315                 320 gct gag tgc gtg gct gat aac tgc gtc taagaccaga gccccgcagc           1245
    Ala Glu Cys Val Ala Asp Asn Cys Val
                    325                 330 ccctggggcc ccccggagcc atggggtgtc ggggctcct gtgcaggctc atgctgcagg    1305
    cggccgaggg cacaggggt ttcgcgctgc tcctgaccgc ggtgaggccg cgccgaccat    1365
    ctctgcactg aagggccctc tggtggccgg cacgggcatt gggaaacagc ctcctccttt   1425
    cccaaccttg cttcttaggg gccccgtgt cccgtctgct ctcagcctcc tcctcctgca    1485
    ggataaagtc atccccaagg ctccagctac tctaaattat gtctccttat aagttattgc   1545
    tgctccagga gattgtcctt catcgtccag gggcctggct cccacgtggt tgcagatacc   1605
    tcagacctgg tgctctaggc tgtgctgagc ccactctccc gagggcgcat ccaagcgggg   1665
    gccacttgag aagtgaataa atggggcggt ttcggaagcg tcnttgtttc nccnggcccc   1725
    ggatctctct gcgtttgaat aaagaatatc tctgttgctc aaaaaaaaaa aaaa         1779
```

FIG. 2B

SEQUENCE LISTING

```
<160> NUMBER OF SEQ ID NOS: 5

<210> SEQ ID NO 1
<211> LENGTH: 1779
<212> TYPE: DNA
<213> ORGANISM: Homo sapiens
<220> FEATURE:
<221> NAME/KEY: CDS
<222> LOCATION: (236)...(1225)
<221> NAME/KEY: misc_feature
<222> LOCATION: (1)...(1779)
<223> OTHER INFORMATION: n = A,T,C or G

<400> SEQUENCE: 1
tgggcagggc gagttgggaa agcggcagcc cccgccgccc ccgcagcccc ttctcctctt      60
tctcccacgt cctatctgcc tctcgctgga ggccaggccg tgcagcatcg aagacaggag    120
gaactggagc ctcattggcc ggcccggggc gccggcctcg ggcttaaata ggagctccgg    180
gctctggctg ggacccgacc gctgccggcc gcgctcccgc tgctcctgcc gggtg atg    238
                                                                 Met
                                                                   1 gaa aac ccc agc ccg gcc gcc gcc ctg ggc aag gcc ctc tgc gct ctc    286
```

-continued

```
                Glu Asn Pro Ser Pro Ala Ala Ala Leu Gly Lys Ala Leu Cys Ala Leu
                                 5                  10                  15 ctc ctg gcc act ctc ggc gcc gcc ggc cag cct ctt ggg gga gag tcc        334
Leu Leu Ala Thr Leu Gly Ala Ala Gly Gln Pro Leu Gly Gly Glu Ser
             20                  25                  30 atc tgt tcc gcc aga gcc ccg gcc aaa tac agc atc acc ttc acg ggc        382
Ile Cys Ser Ala Arg Ala Pro Ala Lys Tyr Ser Ile Thr Phe Thr Gly
 35                  40                  45 aag tgg agc cag acg gcc ttc ccc aag cag tac ccc ctg ttc cgc ccc        430
Lys Trp Ser Gln Thr Ala Phe Pro Lys Gln Tyr Pro Leu Phe Arg Pro
 50                  55                  60                  65 cct gcg cag tgg tct tcg ctg ctg ggg gcc gcg cat agc tcc gac tac        478
Pro Ala Gln Trp Ser Ser Leu Leu Gly Ala Ala His Ser Ser Asp Tyr
             70                  75                  80 agc atg tgg agg aag aac cag tac gtc agt aac ggg ctg cgc gac ttt        526
Ser Met Trp Arg Lys Asn Gln Tyr Val Ser Asn Gly Leu Arg Asp Phe
             85                  90                  95 gcg gag cgc ggc gag gcc tgg gcg ctg atg aag gag atc gag gcg gcg        574
Ala Glu Arg Gly Glu Ala Trp Ala Leu Met Lys Glu Ile Glu Ala Ala
            100                 105                 110 ggg gag gcg ctg cag agc gtg cac gag gtg ttt tcg gcg ccc gcc gtc        622
Gly Glu Ala Leu Gln Ser Val His Glu Val Phe Ser Ala Pro Ala Val
        115                 120                 125 ccc agc ggc acc ggg cag acg tcg gcg gag ctg gag gtg cag cgc aag        670
Pro Ser Gly Thr Gly Gln Thr Ser Ala Glu Leu Glu Val Gln Arg Lys
130                 135                 140                 145 cac tcg ctg gtc tcg ttt gtg gtg cgc atc gtg ccc agc ccc gac tgg        718
His Ser Leu Val Ser Phe Val Val Arg Ile Val Pro Ser Pro Asp Trp
            150                 155                 160 ttc gtg ggc gtg gac agc ctg gac ctg tgc gac ggg gac cgt tgg cgg        766
Phe Val Gly Val Asp Ser Leu Asp Leu Cys Asp Gly Asp Arg Trp Arg
            165                 170                 175 gaa cag gcg gcg ctt gac ctg tac ccc tac gac gcc ggg acg gac agc        814
Glu Gln Ala Ala Leu Asp Leu Tyr Pro Tyr Asp Ala Gly Thr Asp Ser
        180                 185                 190 ggc ttc acc ttc tcc tcc ccc aac ttc gcc acc atc ccg cag gac acg        862
Gly Phe Thr Phe Ser Ser Pro Asn Phe Ala Thr Ile Pro Gln Asp Thr
    195                 200                 205 gtg acc gag ata acg tcc tcc tct ccc agc cac ccg gcc agc tcc ttc        910
Val Thr Glu Ile Thr Ser Ser Ser Pro Ser His Pro Ala Ser Ser Phe
210                 215                 220                 225 tac tac ccg cgg ctg aag gcc tgc tcc cat cgc cag ggt gac act ggt        958
Tyr Tyr Pro Arg Leu Lys Ala Cys Ser His Arg Gln Gly Asp Thr Gly
            230                 235                 240 gcg gct gcg aca gag ccc cag ggc ctt cat ccc tcc cgc ccc agt cct       1006
Ala Ala Ala Thr Glu Pro Gln Gly Leu His Pro Ser Arg Pro Ser Pro
            245                 250                 255 gcc cag cag gac aat gcg ctt gta gac agc gcc tca gtt cca gaa aca       1054
Ala Gln Gln Asp Asn Ala Leu Val Asp Ser Ala Ser Val Pro Glu Thr
        260                 265                 270 ccg ctg gac tgc gag gtc tcc ctg tgg tcg tcc tgg gga ctg tgc gga       1102
Pro Leu Asp Cys Glu Val Ser Leu Trp Ser Ser Trp Gly Leu Cys Gly
    275                 280                 285 ggc cac tgt ggg agg ctc ggg tcc aag agc agg act ccg tac gcc cgg       1150
Gly His Cys Gly Arg Leu Gly Ser Lys Ser Arg Thr Pro Tyr Ala Arg
290                 295                 300                 305 gtc cag ccc gcc aac aac ggg agc ccc tgc ccc gag ctc gaa gaa gag       1198
Val Gln Pro Ala Asn Asn Gly Ser Pro Cys Pro Glu Leu Glu Glu Glu
            310                 315                 320
```

-continued

```
gct gag tgc gtg gct gat aac tgc gtc taagaccaga gccccgcagc        1245
Ala Glu Cys Val Ala Asp Asn Cys Val
        325                 330 ccctggggcc ccccggagcc atgggtgtc gggggctcct gtgcaggctc atgctgcagg  1305
cggccgaggg cacagggggt ttcgcgctgc tcctgaccgc ggtgaggccg cgccgaccat  1365
ctctgcactg aagggccctc tggtggccgg cacgggcatt gggaaacagc ctcctccttt  1425
cccaaccttg cttcttaggg gccccgtgt cccgtctgct ctcagcctcc tcctcctgca   1485
ggataaagtc atccccaagg ctccagctac tctaaattat gtctccttat aagttattgc  1545
tgctccagga gattgtcctt catcgtccag gggcctggct cccacgtggt tgcagatacc  1605
tcagacctgg tgctctaggc tgtgctgagc ccactctccc gagggcgcat ccaagcgggg  1665
gccacttgag aagtgaataa atgggcggt ttcggaagcg tcnttgtttc nccnggcccc   1725
ggatctctct gcgtttgaat aaagaatatc tctgttgctc aaaaaaaaaa aaaa         1779
```

<210> SEQ ID NO 2
<211> LENGTH: 330
<212> TYPE: PRT
<213> ORGANISM: Homo sapiens

<400> SEQUENCE: 2

```
Met Glu Asn Pro Ser Pro Ala Ala Ala Leu Gly Lys Ala Leu Cys Ala
  1               5                  10                  15

Leu Leu Leu Ala Thr Leu Gly Ala Ala Gly Gln Pro Leu Gly Gly Glu
             20                  25                  30

Ser Ile Cys Ser Ala Arg Ala Pro Ala Lys Tyr Ser Ile Thr Phe Thr
         35                  40                  45

Gly Lys Trp Ser Gln Thr Ala Phe Pro Lys Gln Tyr Pro Leu Phe Arg
     50                  55                  60

Pro Pro Ala Gln Trp Ser Ser Leu Leu Gly Ala Ala His Ser Ser Asp
 65                  70                  75                  80

Tyr Ser Met Trp Arg Lys Asn Gln Tyr Val Ser Asn Gly Leu Arg Asp
                 85                  90                  95

Phe Ala Glu Arg Gly Glu Ala Trp Ala Leu Met Lys Glu Ile Glu Ala
            100                 105                 110

Ala Gly Glu Ala Leu Gln Ser Val His Glu Val Phe Ser Ala Pro Ala
        115                 120                 125

Val Pro Ser Gly Thr Gly Gln Thr Ser Ala Glu Leu Glu Val Gln Arg
    130                 135                 140

Lys His Ser Leu Val Ser Phe Val Val Arg Ile Val Pro Ser Pro Asp
145                 150                 155                 160

Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
            180                 185                 190

Ser Gly Phe Thr Phe Ser Ser Pro Asn Phe Ala Thr Ile Pro Gln Asp
        195                 200                 205

Thr Val Thr Glu Ile Thr Ser Ser Pro Ser His Pro Ala Ser Ser
    210                 215                 220

Phe Tyr Tyr Pro Arg Leu Lys Ala Cys Ser His Arg Gln Gly Asp Thr
225                 230                 235                 240

Gly Ala Ala Ala Thr Glu Pro Gln Gly Leu His Pro Ser Arg Pro Ser
                245                 250                 255

Pro Ala Gln Gln Asp Asn Ala Leu Val Asp Ser Ala Ser Val Pro Glu
```

```
                260                  265                  270
Thr Pro Leu Asp Cys Glu Val Ser Leu Trp Ser Ser Trp Gly Leu Cys
            275                  280                  285

Gly Gly His Cys Gly Arg Leu Gly Ser Lys Ser Arg Thr Pro Tyr Ala
        290                  295                  300

Arg Val Gln Pro Ala Asn Asn Gly Ser Pro Cys Pro Glu Leu Glu Glu
305                  310                  315                  320

Glu Ala Glu Cys Val Ala Asp Asn Cys Val
                325                  330

<210> SEQ ID NO 3
<211> LENGTH: 37
<212> TYPE: PRT
<213> ORGANISM: Homo sqpiens

<400> SEQUENCE: 3

Ala Gln Gln Asp Asn Ala Leu Val Asp Ser Ala Ser Val Pro Glu Thr
  1               5                  10                  15

Pro Leu Asp Cys Glu Val Ser Leu Trp Ser Ser Trp Glu Leu Cys Gly
             20                  25                  30

Gly His Cys Gly Arg
             35

<210> SEQ ID NO 4
<211> LENGTH: 21
<212> TYPE: DNA
<213> ORGANISM: Homo sapiens

<400> SEQUENCE: 4
actcttgctt ggacgagctc t                                        21

<210> SEQ ID NO 5
<211> LENGTH: 23
<212> TYPE: DNA
<213> ORGANISM: Homo sapiens

<400> SEQUENCE: 5
actgagaacg aacctgctcg aga                                      23
```

NPG-1 GENE THAT IS DIFFERENTIALLY EXPRESSED IN PROSTATE TUMORS

RELATED APPLICATIONS

This application is a continuation-in-part of U.S. Ser. No. 09/022,238, filed Feb. 11, 1998, which is a continuation-in-part of U.S. Ser. No. 08/644,326, filed May 10, 1996, U.S. Pat. No. 5,804,382 the contents of which are herein incorporated by reference.

This invention was made with Government support under NIH grant NIH DK 38841 and F32DK 09364 and a U.S. Navy grant N00014-930776.

BACKGROUND OF THE INVENTION

Prostate growth, from normal to neoplastic, can be viewed as a change from paracrine regulation of epithelial growth to autocrine regulation (Culig et al. (1996) *The Prostate* 28: 392–405). Additionally, prostate cancers, especially advanced tumors, are frequently insensitive to the normal mitogenic action of growth factors, suggesting that prostate cancer expresses constitutively one or more of those genes unregulated by growth factors. The identification of genes expressed differentially in prostate cancers of dissimilar phenotypes could give clues to genes important in malignant transformation and progression. Moreover, these genes could serve as prognostic and diagnostic markers as well as new targets for therapy. However, the identification of growth regulatory genes in prostate cancer has been difficult and has lagged behind comparable studies in other cell types.

Methods to identify differentially expressed genes in other tissues have included differential screening of cDNA, libraries with selective probes, subtractive hybridization utilizing DNA/DNA hybrids or DNA/RNA hybrids, RNA fingerprinting and differential display (Mather et al. (1981) *Cell* 23:369–378; Hedrick et al. (1984) *Nature* 308:149–153; Davis et al. (1992) *Cell* 51:987–1000; Welsh et al. (1992) *Nucleic Acids Res.* 20:4965–4970; and Liang and Pardee (1992) *Science* 257:967–971). Recently, PCR-coupled subtractive processes have also been reported (Straus and Ausubel (1990) *Proc. Natl. Sci. USA* 87:1889–1893; Sive and John (1988) *Nucleic Acids Res.* 16:10937; Wieland et al. (1990) *Proc. Natl. Acad. USA* 87:2720–2724; Wang and Brown (1991) *Proc. Natl. Acad Sci. USA* 88:11505–11509; Lisitsyn et al. (1993) *Science* 259:946–951; Zing et al. (1994) *Nucleic Acids Res.* 22:4381–4385; Hubank and Schak (1994) *Nucleic Acids Res.* 22:5640–5648). Each of these methods has achieved some success but each has some inherent limitations. For example, problems associated with differential display include identification of "false positives," redundancy, and under-representation of certain mRNA species. Liang and Pardee (1992) *Science* 257:967–971. In addition, cDNA-RDA (Hubank and Schatz (1994) *Nucleic Acids Res.* 22:5640–5648; Lisitsyn et al. (1993) *Science* 259:946–951) is a labor-intensive process, and its efficiency remains to be evaluated. Some advances have been made in isolating genes expressed preferentially in prostate cancer versus normal tissue (Shen et al. (1995) *PNAS USA* 92:6778–6782; Wang et al. (1996) *Cancer Res.* 56:3634–3637; Liu et al. (1997) *The Prostate* 30:145–153). Less data exist regarding differential expression of novel genes in human prostate cancers of different growth and metastatic potential (Blok et al. (1995) *The Prostate* 26:213–224).

Thus, a need still exists to develop a more efficient method for identification of differentially expressed genes and differences in genomic sequences.

Accordingly, an object of the invention is to provide a differentially expressed gene isolated by the methods described herein.

SUMMARY OF THE INVENTION

The transition from androgen-dependent to aggressive androgen-independent growth is an important development in prostate cancer, and the identification of genes expressed differentially between these two phenotypes can provide new therapeutic targets as well as prognostic markers.

The inventors have developed a novel method termed "Linker Capture Subtraction" (LCS), which overcomes many of the problems associated with present methods for identifying differentially expressed genes and differences in genomic sequences. Unlike other methods such as representational difference analysis (RDA) (Hubank and Schatz (1994) *Nucleic Acids Res.* 22:5640–5648; Lisitsyn et. al. (1993) *Science* 259:946–951) LCS is a subtraction method coupled to PCR amplification which does not rely on a kinetic mechanism of enrichment of selected sequences. Rather, LCS achieves enrichment by specifically preserving PCR-priming sites of target sequences, using a nuclease which digests single-stranded nucleic acid as the mediator. Moreover, LCS is also a less labor-intensive process.

Using LCS, several genes expressed differentially between the human prostate carcinoma cell lines LNCaP and PC-3, which are androgen-dependent and androgen-independent, respectively, have now been isolated. One of these genes, designated NPG-1, was expressed by the majority of primary tumors examined. Moreover, the degree of NPG-1 expressed correlated with an aggressive histopathology.

Accordingly, the invention pertains to isolated nucleic acid molecules (e.g., cDNAs) comprising a nucleotide sequence encoding a secretory NPG-1 protein or biologically active portions thereof, as well as nucleic acid fragments suitable as primers or hybridization probes for the detection of NPG-1-encoding nucleic acid (e.g., mRNA). In particularly preferred embodiments, the isolated nucleic acid molecule comprises the nucleotide sequence of SEQ ID NO:1, or the coding region or a complement of this nucleotide sequence. In other particularly preferred embodiments, the isolated nucleic acid molecule of the invention comprises a nucleotide sequence which hybridizes to or is at least about 80%, 85%, 90%, 95%, or 98% or more homologous to the entire nucleotide sequence shown in SEQ ID NO: 1, or a portion of this sequence. In other preferred embodiments, the isolated nucleic acid molecule encodes the amino acid sequence of SEQ ID NO:2. The preferred NPG-1 proteins of the present invention also preferably possess at least one of the NPG-1 activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2, e.g., sufficiently homologous to an amino acid sequence of SEQ ID NO:2 such that the protein or portion thereof maintains an NPG-1 activity. Preferably, the protein or portion thereof encoded by the nucleic acid molecule maintains the ability to modulate tumor cell adhesion, e.g., malignant prostate cell adhesion, or the ability to modulate adhesion, growth and regeneration of neurons. In one embodiment, the protein encoded by the nucleic acid molecule is at least 80%, 85%, 90%, 95%, or 98% or more homologous to the amino acid sequence of SEQ ID NO:2. A portion or fragment of NPG-1 can be a polypeptide of at least 5, 10, 20, 50, 100, 150, 170, 200, 250, 300, 320 amino acids in length; at least 5, preferably at least 10, more preferably at least 20, most preferably at least 50, 100, 150, 200, 210, 250, 300, or 320 contiguous amino acids from SEQ ID NO:2. In a preferred embodiment; a fragment is at least 4, 5, 10, 15, 20, 25 amino acids in length, but no more than 100 amino acids in length.

In another embodiment, the isolated nucleic acid molecule encodes a NPG-1 protein which differs from the amino acid sequence of SEQ ID NO:2 by at least but not more than 1, 2, 3, 5, 8, 10, 20 amino acid residues.

In yet another embodiment, the isolated nucleic acid molecule is derived from a human and encodes a portion of a protein which includes a type I thrombospondin repeat domain. Preferably, the type I thrombospondin repeat domain encoded by the human nucleic acid molecule is at least about 80%, 85%, 90%, 95%, or 98% or more homologous to the type I thrombospondin repeat domain (i.e., amino acid residues 258–294) of SEQ ID NO:2 which is shown as a separate sequence designated SEQ ID NO:3.

In another preferred embodiment, the isolated nucleic acid molecule is derived from a human and encodes a protein (e.g., an NPG-1 fusion protein) which includes a type I thrombospondin repeat domain which is at least about 80% or more homologous to SEQ ID NO:3 and has one or more of the following activities: 1) it can bind to the extracellular matrix, e.g., the basal lamina; 2) it can interact with a growth factor, e.g., VEGF; 3) it can interact with a cytokine; 4) it can modulate tumor cell adhesion; 5) it can modulate tumor cell invasion; 6) it can modulate tumor cell migration; 7) it can modulate tumor metastasis; 8) it can modulate tumor angiogenesis; 9) it can modulate extracellular matrix degradation, e.g., via tumor secreted proteases; 10) it can modulate cell proliferation; 11) it can modulate tissue architecture and differentiation, e.g., cellular architecture and differentiation; 12) it can modulate adhesion and outgrowth of embryonic neurons; 13) it can modulate the attachment of neurons; 14) it can modulate, e.g., stimulate, the growth of nerve cells; and 15) it can modulate the regeneration of nerve cell growth.

In another embodiment, the isolated nucleic acid molecule is at least 15 nucleotides in length and hybridizes under stringent conditions to a nucleic acid molecule comprising the nucleotide sequence of SEQ ID NO:1. Preferably, the isolated nucleic acid molecule corresponds to a naturally occurring nucleic acid molecule. More preferably, the isolated nucleic acid encodes naturally occurring human NPG-1 or a biologically active portion thereof. Moreover, given the disclosure herein of an NPG-1-encoding cDNA sequence (e.g., SEQ ID NO:1), antisense nucleic acid molecules (i.e., molecules which are complementary to the coding strand of the NPG-1 cDNA sequence) are also provided by the invention.

Another aspect of the invention pertains to vectors, e.g., recombinant expression vectors, containing the nucleic acid molecules of the invention and host cells into which such vectors have been introduced. In one embodiment, such a host cell is used to produce NPG-1 protein by culturing the host cell in a suitable medium. If desired, the NPG-1 protein can be then isolated from the medium or the host cell.

Yet another aspect of the invention pertains to transgenic nonhuman animals in which an NPG-1 gene has been introduced or altered. In one embodiment, the genome of the nonhuman animal has been altered by introduction of a nucleic acid molecule of the invention encoding NPG-1 as a transgene. In another embodiment, an endogenous NPG-1 gene within the genome of the non-human animal has been altered, e.g., functionally disrupted, by homologous recombination.

Still another aspect of the invention pertains to an isolated NPG-1 protein or a portion, e.g., a biologically active portion, thereof. In a preferred embodiment, the isolated NPG-1 protein or portion thereof can modulate tumor cell adhesion. In another preferred embodiment, the isolated NPG-1 protein or portion thereof is sufficiently homologous to an amino acid sequence of SEQ ID NO:2 such that the protein or portion thereof maintains the ability to modulate tumor cell adhesion.

In one embodiment, the biologically active portion of the NPG-1 protein includes a domain or motif, preferably a domain or motif which has an NPG-1 activity. The domain can be a type I thrombospondin repeat domain. If the active portion of the protein which comprises type I thrombospondin repeat domain is isolated or derived from a human, it is preferred that the type I thrombospondin repeat domain be at least about 80%, 85%, 90%, 95%, or 98% or more homologous to SEQ ID NO:3. Preferably, the biologically active portion of the NPG-1 protein which includes a type I thrombospondin repeat domain also has one or more of the following activities: 1) it can bind to the extracellular matrix, e.g., the basal lamina; 2) it can interact with a growth factor, e.g., VEGF; 3) it can interact with a cytokine; 4) it can modulate tumor cell adhesion; 5) it can modulate tumor cell invasion; 6) it can modulate tumor cell migration; 7) it can modulate tumor metastasis; 8) it can modulate tumor angiogenesis; 9) it can modulate extracellular matrix degradation, e.g., via tumor secreted proteases; 10) it can modulate cell proliferation; 11) it can modulate tissue architecture and differentiation, e.g., cellular architecture and differentiation; 12) it can modulate adhesion and outgrowth of embryonic neurons; 13) it can modulate the attachment of neurons; 14) it can modulate, e.g., stimulate, the growth of nerve cells; and 15) it can modulate the regeneration of nerve cell growth.

The invention also provides an isolated preparation of an NPG-1 protein. In preferred embodiments, the NPG-1 protein comprises the amino acid sequence of SEQ ID NO:2. In another preferred embodiment, the invention pertains to an isolated protein which is substantially homologous to the entire amino acid sequence of SEQ ID NO:2. In yet another embodiment, the protein is at least about 76%, 80%, 85%, 90%, 95%, or 98% or more homologous to the entire amino acid sequence of SEQ ID NO:2. In other embodiments, the isolated NPG-1 protein comprises an amino acid sequence which is at least about 76% or 80% or more homologous to the amino acid sequence of SEQ ID NO:2 and has one or more of the following activities: 1) it can bind to the extracellular matrix, e.g., the basal lamina; 2) it can interact with a growth factor, e.g., VEGF; 3) it can interact with a cytokine; 4) it can modulate tumor cell adhesion; 5) it can modulate tumor cell invasion; 6) it can modulate tumor cell migration; 7) it can modulate tumor metastasis; 8) it can modulate tumor angiogenesis; 9) it can modulate extracellular matrix degradation, e.g., via tumor secreted proteases; 10) it can modulate cell proliferation; 11) it can modulate tissue architecture and differentiation, e.g., cellular architecture and differentiation; 12) it can modulate adhesion and outgrowth of embryonic neurons; 13) it can modulate the attachment of neurons; 14) it can modulate, e.g., stimulate, the growth of nerve cells; and 15) it can modulate the regeneration of nerve cell growth.

In another embodiment, the isolated NPG-1 protein differs from the amino acid sequence of SEQ ID NO:2 by at least but not more than 1, 2, 3, 5, 8, 10, 20 amino acid residues.

Alternatively, the isolated NPG-1 protein can comprise an amino acid sequence which is encoded by a nucleotide sequence which hybridizes, e.g., hybridizes under stringent conditions, or is at least about 80%, 85%, 90%, 95%, or 98% or more homologous to the nucleotide sequence of SEQ ID NO:1. It is also preferred that the preferred forms of NPG-1 also have one or more of the NPG-1 activities described herein.

The NPG-1 protein (or polypeptide) or a biologically active portion thereof can be operatively linked to a non-NPG-1 polypeptide to form a fusion protein. In addition, the NPG-1 protein or a biologically active portion thereof can be incorporated into a pharmaceutical composition comprising the protein and a pharmaceutically acceptable carrier.

The NPG-1 protein of the invention, or portions or fragments thereof, can be used to prepare anti-NPG-1 antibodies. Accordingly, the invention also provides an antigenic peptide of NPG-1 which comprises at least 8 amino acid residues of the amino acid sequence shown in SEQ ID NO:2 and encompasses an epitope of NPG-1 such that an antibody raised against the peptide forms a specific immune complex with NPG-1. Preferably, the antigenic peptide comprises at least 10 amino acid residues, more preferably at least 15 amino acid residues, even more preferably at least 20 amino acid residues, and most preferably at least 30 amino acid residues. The invention further provides an antibody that specifically binds NPG-1. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention pertains to methods for modulating a cell-associated activity, e.g., proliferation or differentiation. Such methods include contacting the cell with an agent which modulates NPG-1 protein activity or NPG-1 nucleic acid expression such that a cell associated activity is altered relative to a cell associated activity (e.g., the same cell associated activity) of the cell in the absence of the agent. In a preferred embodiment, the cell is a tumor cell, e.g., a malignant prostate cell. The agent which modulates NPG-1 activity can be an agent which stimulates NPG-1 protein activity or NPG-1 nucleic acid expression. Examples of agents which stimulate NPG-1 protein activity or NPG-1 nucleic acid expression include small molecules, active NPG-1 proteins, and nucleic acids encoding NPG-1 that have been introduced into the cell. Examples of agents which inhibit NPG-1 activity or expression include small molecules, antisense NPG-1 nucleic acid molecules, and antibodies that specifically bind to NPG-1. In a preferred embodiment, the cell is present within a subject and the agent is administered to the subject.

The present invention also pertains to methods for treating subjects having various disorders. For example, the invention pertains to methods for treating a subject having a disorder characterized by aberrant NPG-1 protein activity or nucleic acid expression such as a tumor, e.g., a malignant or benign prostate tumor. These methods include administering to the subject an NPG-1 modulator (e.g., a small molecule) such that treatment of the subject occurs.

In another embodiment, the invention pertains to methods for treating a subject having a tumor, e.g., a malignant or benign prostate tumor, squamous carcinoma, melanoma, glioma, osteosarcoma, or breast adenocarcinoma, comprising administering to the subject an NPG-1 modulator such that treatment occurs.

In other embodiments, the invention pertains to methods for treating a subject having a tumor, e.g., a malignant or benign prostate tumor, comprising administering to the subject an NPG-1 protein or portion thereof such that treatment occurs. Tumors can also be treated according to the invention by administering to the subject having the disorder a nucleic acid encoding an NPG-1 protein or portion thereof such that treatment occurs.

NPG-1 is also useful for adhesion and outgrowth of axon. The invention also pertains to a method of attaching a nerve cell to a matrix including contacting the matrix with a nerve cell and NPG-1 at a concentration effective to effect attachment of cells to the matrix.

The invention also provides a method of stimulating growth of a nerve cell including contacting a nerve cell with NPG-1 at a concentration effective to stimulate growth of a nerve cell.

The invention further pertains to a method of regenerating nerve cells in a subject including administering to a subject NPG-1 at a concentration effective to regenerate nerve cells in a subject.

The invention also pertains to methods for detecting genetic lesions in an NPG-1 gene, thereby determining if a subject with the lesioned gene is at risk for (or is predisposed to have) a disorder characterized by aberrant or abnormal NPG-1 nucleic acid expression or NPG-1 protein activity, e.g., a malignant disorder such as prostate cancer. In preferred embodiments, the methods include detecting, in a sample of cells from the subject, the presence or absence of a genetic lesion characterized by an alteration affecting the integrity of a gene encoding an NPG-1 protein, or the misexpression of the NPG-1 gene.

Another aspect of the invention pertains to methods for detecting the presence of NPG-1 in a biological sample. In a preferred embodiment, the methods involve contacting a biological sample (e.g., a prostate tissue sample) with a compound or an agent capable of detecting NPG-1 protein or NPG-1 mRNA such that the presence of NPG-1 is detected in the biological sample. The compound or agent can be, for example, a labeled or labelable nucleic acid probe capable of hybridizing to NPG-1 mRNA or a labeled or labelable antibody capable of binding to NPG-1 protein. The invention further provides methods for diagnosis of a subject with, for example, a proliferative disorder, e.g., a malignant disorder such as prostate cancer, based on detection of NPG-1 protein or mRNA. In one embodiment, the method involves contacting a cell or a biological sample, e.g., a blood, urine, or tissue sample (e.g., a prostate tissue sample) from the subject with an agent capable of detecting NPG-1 protein or mRNA, determining the amount of NPG-1 protein or mRNA expressed in the cell or tissue sample, comparing the amount of NPG-1 protein or mRNA expressed in the cell or tissue sample to a control sample and forming a diagnosis based on the amount of NPG-1 protein or mRNA expressed in the cell or tissue sample as compared to the control sample. Preferably, the cell sample is a prostate tissue sample. Kits for detecting NPG-1 in a biological sample are also within the scope of the invention.

Still another aspect of the invention pertains to methods, e.g., screening assays, for identifying a compound for treating a disorder characterized by aberrant NPG-1 nucleic acid expression or protein activity, e.g., a malignant disorder such as prostate cancer. These methods typically include assaying the ability of the compound or agent to modulate the expression of the NPG-1 gene or the activity of the NPG-1 protein thereby identifying a compound for treating a disorder characterized by aberrant NPG-1 nucleic acid expression or protein activity. In a preferred embodiment, the method involves contacting a biological sample, e.g., a cell or tissue sample, e.g., a prostate tissue sample, obtained from a subject having the disorder with the compound or agent, determining the amount of NPG-1 protein expressed and/or measuring the activity of the NPG-1 protein in the biological sample, comparing the amount of NPG-1 protein expressed in the biological sample and/or the measurable NPG-1 biological activity in the cell to that of a control sample. An alteration in the amount of NPG-1 protein expression or NPG-1 activity in the cell exposed to the compound or agent in comparison to the control is indicative of a modulation of NPG-1 expression and/or NPG-1 activity.

The invention also pertains to methods for identifying a compound or agent which interacts with (e.g., binds to) an NPG-1 protein. These methods can include the steps of contacting the NPG-1 protein with the compound or agent under conditions which allow binding of the compound to the NPG-1 protein to form a complex and detecting the formation of a complex of the NPG-1 protein and the compound in which the ability of the compound to bind to the NPG-1 protein is indicated by the presence of the compound in the complex.

The invention further pertains to methods for identifying a compound or agent which modulates, e.g., stimulates or inhibits, the interaction of the NPG-1 protein with a target molecule, e.g., an extracellular matrix component such as, for example, an extracellular matrix protein. In these methods, the NPG-1 protein is contacted, in the presence of the compound or agent, with the target molecule under conditions which allow binding of the target molecule to the NPG-1 protein to form a complex. An alteration, e.g., an increase or decrease, in complex formation between the NPG-1 protein and the target molecule as compared to the amount of complex formed in the absence of the compound or agent is indicative of the ability of the compound or agent to modulate the interaction of the NFG-1 protein with a target molecule.

BRIEF DESCRIPTION OF THE DRAWINGS

FIG. 2 is a depiction of the human NPG-1 nucleotide (SEQ ID NO: 1) and the NPG-1 amino acid (SEQ ID NO:2) sequences.

Figure 1:
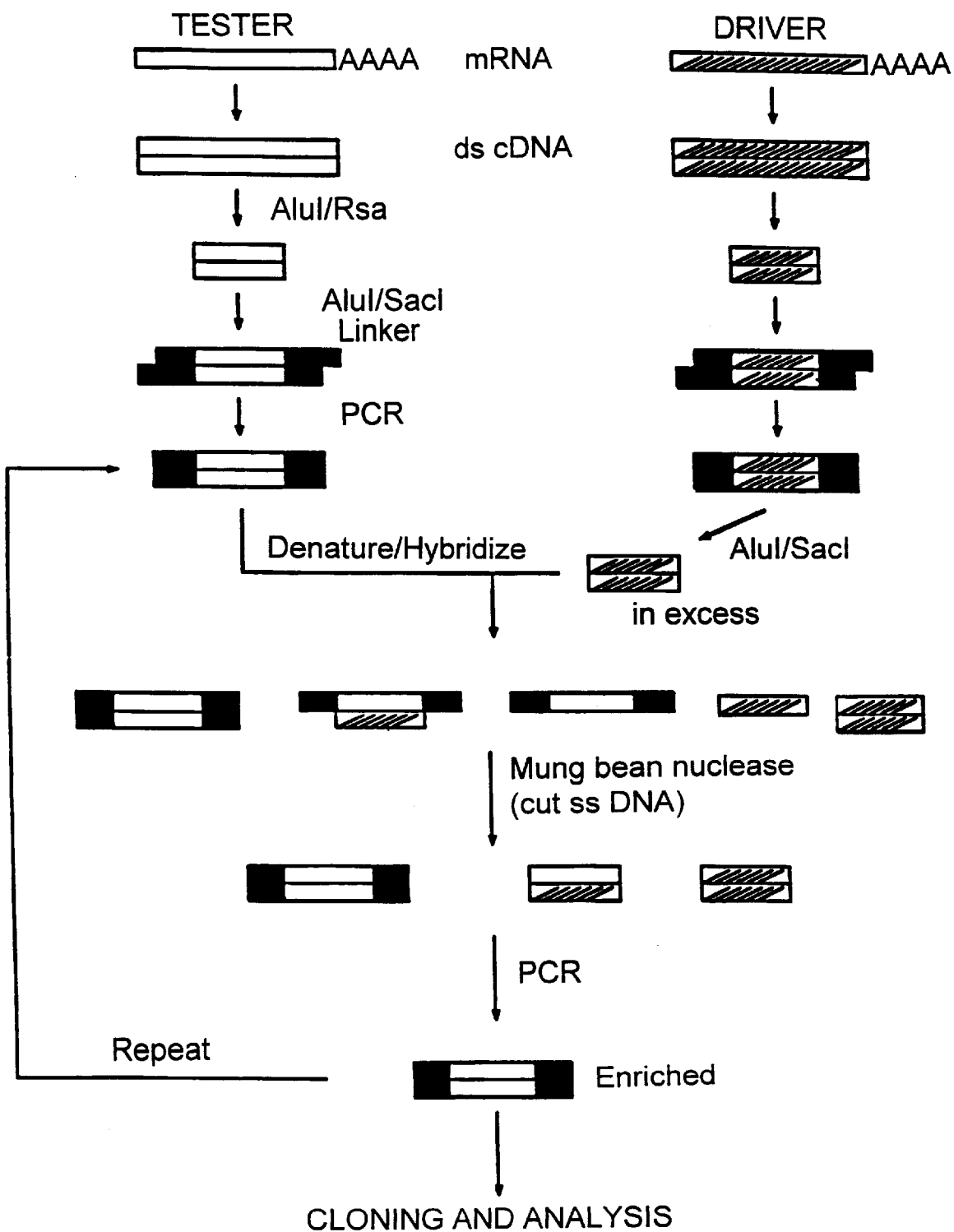
FIG. 1 is a schematic diagram of the Linker Capture Subtraction method for identifying differentially expressed genes and differences in genomic nucleic acid sequences.

The following sections are intended to provide one of ordinary skill in the art with general guidance in making and using the claimed invention.

DESCRIPTION OF THE INVENTION

I. NPG-1

Prostate growth, from normal to neoplastic, can be viewed as a change from paracrine regulation of epithelial growth to autocrine regulation (Culig Z. et al. (1996) *The Prostate*, 28:392–405). Additionally, prostate cancers, especially advanced tumors, are frequently insensitive to the normal mitogenic action of growth factors, suggesting that prostate cancer expresses constitutively one or more of those genes unregulated by growth factors. The identification of genes expressed differentially in prostate cancers of dissimilar phenotypes could give clues to genes important in malignant transformation and progression. As described herein, a novel gene NPG-1 was identified and isolated according to the method of the invention. A entire sequence of this novel gene is set forth in the sequence listing as SEQ ID NO:1 and the corresponding amino acid sequence is set forth as SEQ ID NO:2.

The nucleic acid sequence of the human NPG-1 was used as a database query using the BLASTS program (BLASTN1. 4.11MP, Altschul et al. (1990) *J. Mol. Biol.* 215:403). The closest hits were to the MINDIN (GenBank™ Accession Number AB006085) and to the MINDIN (GenBank™ Accession Number AB006084) genes, which are also described in Higashijima S., et al. (1997) *Developmental Biol.* 192:211–227.

II. Isolated Nucleic Acid Molecules

One aspect of the invention pertains to isolated nucleic acid molecules that encode NPG-1 or biologically active portions thereof, as well as nucleic acid fragments sufficient for use as hybridization probes to identify NPG-1-encoding nucleic acid (e.g., NPG-1 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NPG-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a prostate cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having he nucleotide sequence of SEQ ID NO:1, or a portion thereof, can be isolated using standard molecular biology techniques and the sequence information provided herein. For example, a mouse NPG-1 cDNA can be isolated from a mouse prostate cancer library using all or portion of SEQ ID NO:1 as a hybridization probe and standard hybridization techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO:1 can be isolated by the polymerase chain reaction using oligonucleotide primers designed based upon the sequence of SEQ ID NO:1. For example, mRNA can be isolated from normal prostate cells (e.g., by the guanidinium-thiocyanate extraction procedure of Chirgwin et al. (1979) *Biochemistry* 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an NPG-1 nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1 . The sequence of SEQ ID NO:1 corresponds to the human NPG-1 cDNA. This cDNA comprises sequences encoding the NPG-1 protein (i.e., "the coding region", from nucleotides 235 to 1225).

In another preferred embodiment, an isolated nucleic acid molecule of the invention comprises a nucleic acid molecule which is a complement of the nucleotide sequence shown in SEQ ID NO:1 or a portion of this nucleotide sequence. A nucleic acid molecule which is complementary to the nucleotide sequence shown in SEQ ID NO:1 is one which is sufficiently complementary to the nucleotide sequence shown in SEQ ID NO:1 such that it can hybridize to the nucleotide sequence shown in SEQ ID NO:1, thereby forming a stable duplex.

In still another preferred embodiment, an isolated nucleic acid molecule of the invention comprises a nucleotide sequence which is at least about 80%, 85%, 90%, 95%, or 98% or more homologous to the entire nucleotide sequence shown in SEQ ID NO:1 or a portion of this nucleotide sequence. In an additional preferred embodiment, an isolated nucleic acid molecule of the invention comprises a nucleotide sequence which hybridizes, e.g., hybridizes under stringent conditions, to the nucleotide sequence shown in SEQ ID NO:1 or a portion of this nucleotide sequence.

Moreover, the nucleic acid molecule of the invention can comprise only a portion of the coding region of SEQ ID NO:1, for example a fragment which can be used as a probe or primer or a fragment encoding a biologically active portion of NPG-1. The nucleotide sequence determined from the cloning of the NPG-1 gene from a human allows for the generation of probes and primers designed for use in identifying and/or cloning NPG-1 homologues in other cell types, e.g., from other tissues, as well as NPG-1 homologues from other organisms. The probe/primer typically comprises a substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1 sense, an antisense sequence of SEQ ID NO:1, or naturally occurring mutants thereof. Primers based on the nucleotide sequence in SEQ ID NO:1 can be used in PCR reactions to clone NPG-1 homologues. Probes based on the NPG-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an NPG-1 protein, such as by measuring a level of an NPG-1 encoding nucleic acid in a sample of cells from a subject e.g., detecting NPG-1 mRNA levels or determining whether a genomic NPG-1 gene has been mutated or deleted.

In one embodiment, the nucleic acid molecule of the invention encodes a protein or portion thereof which includes an amino acid sequence which is sufficiently homologous to an amino acid sequence of SEQ ID NO:2 such that the protein or portion thereof maintains the ability to modulate tumor cell adhesion, e.g., malignant prostate cell adhesion. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2) amino acid residues to an amino acid sequence of SEQ ID NO:2 such that the protein or portion thereof is able to modulate tumor cell adhesion's. g., malignant prostate cell adhesion or a skilled artisan would clearly recognize it as a non-functional allelic variant of the human NPG-1 protein described herein.

Portions of proteins encoded by the NPG-1 nucleic acid molecule of the invention are preferably biologically active portions of the NPG-1 protein. As used herein, the term "biologically active portion of NPG-1" is intended to include a portion, e.g., a domain/motif, of NPG-1 that has one or more of the following activities: 1) it can bind to the extracellular matrix, e.g., the basal lamina; 2) it can interact with a growth factor, e.g., VEGF; 3) it can interact with a cytokine; 4) it can modulate tumor cell adhesion; 5) it can modulate tumor cell invasion; 6) it can modulate tumor cell migration; 7) it can modulate tumor metastasis; 8) it can modulate tumor angiogenesis; 9) it can modulate extracellular matrix degradation, e.g., via tumor secreted proteases; 10) it can modulate cell proliferation; 11) it can modulate tissue architecture and differentiation, e.g., cellular architecture and differentiation; 12) it can modulate adhesion and outgrowth of embryonic neurons; 13) it can modulate the attachment of neurons; 14) it can modulate, e.g., stimulate, the growth of nerve cells; and 15) it can modulate the regeneration nerve cell growth.

Standard binding assays, e.g., immunoprecipitations and yeast two-hybrid assays as described herein, can be performed to determine the ability of an NPG-1 protein or a biologically active portion thereof to interact with (e.g., bind to) an extracellular matrix protein. To determine whether an NPG-1 protein or a biologically active portion thereof can modulate a response in a tumor cell such as a malignant prostate cell, methods known in the art can be used. For example, to determine whether an NPG-1 protein, or a biologically active portion thereof can modulate tumor cell migration and invasion, the Boyden chamber invasion assay (described in, for example, Wang T. N. et al. (1995) Cancer Res. 36: 75) can be used. Furthermore, to determine whether an NPG-1 protein or a biologically active portion thereof can modulate tumor cell adhesion, fibrin gels can be used as described in, for example, Hosokawa, T. et al. (1993) Oncology. Res. 5:183–189. To determine whether an NPG-1 protein or a biologically active portion thereof can modulate tumor growth and/or metastasis, nude or SCID mice can be subcutaneously or orthotopically (e.g., in the prostate) injected with a tumor. Tumor growth and/or metastasis can then be determined, as described in, for example, Wang, M. et al. (1991) Differentiation 48: 115–125, and Rembrink, K. et al. (1997) *Prostate* 31:168–174.

In one embodiment, the biologically active portion of NPG-1 comprises a type I thrombospondin repeat domain. Preferably, the type I thrombospondin repeat domain is encoded by a nucleic acid molecule derived from a human and is at least about 76%, 80%, 85%, 90%, 95%, or 98% or more homologous to SEQ ID NO:3. In a preferred embodiment, the biologically active portion of the protein which includes the type I thrombospondin repeat domain can modulate tumor cell adhesion, e.g., malignant prostate cell adhesion. In a preferred embodiment, the biologically active portion comprises the type I thrombospondin repeat domain of NPG-1 as represented by amino acid residues 258 to 294 of SEQ ID NO:2 and shown separately as SEQ ID NO:3. Additional nucleic acid fragments encoding biologically active portions of NPG-1 can be prepared by isolating a portion of SEQ ID NO:1, expressing the encoded portion of NPG-1 protein or peptide (e.g., by recombinant expression in vitro) and assessing the activity of the encoded portion of NPG-1 protein or peptide.

The invention further encompasses nucleic acid molecules that differ from the nucleotide sequence shown in SEQ ID NO:1 (and portions thereof) due to degeneracy of the genetic code and thus encode the same NPG-1 protein as that encoded by the nucleotide sequence shown in SEQ ID NO:1. In another embodiment, an isolated nucleic acid molecule of the invention has a nucleotide sequence encoding a protein having an amino acid sequence shown in SEQ ID NO:2. In a still further embodiment, the nucleic acid molecule of the invention encodes a full length human protein which is substantially homologous to the amino acid sequence of SEQ ID NO:2.

In addition to the human NPG-1 nucleotide sequence shown in SEQ ID NO:1, it will be appreciated by those skilled in the art that DNA sequence polymorphisms that lead to changes in the amino acid sequences of NPG-1 may exist within a population (e.g., the human population). Such genetic polymorphism in the NPG-1 gene may exist among individuals within a population due to natural allelic variation. As used herein, the terms "gene" and "recombinant gene" refer to nucleic acid molecules comprising an open reading frame encoding an NPG-1 protein, preferably a human NPG-1 protein. Such natural allelic variations can typically result in 1.5% variance in the nucleotide sequence of the NPG-1 gene. Any and all such nucleotide variations and resulting amino acid polymorphisms in NPG-1 that are the result of natural allelic variation and that do not alter the functional activity of NPG-1 are intended to be within the scope of the invention. Moreover, nucleic acid molecules encoding NPG-1 proteins from other species, and thus which have a nucleotide sequence which differs from the human sequence of SEQ ID NO:1, are intended to be within the scope of the invention. Nucleic acid molecules corresponding to natural allelic variants and nonhuman homologues of the human NPG-1 cDNA of the invention can be isolated based on their homology to the human NPG-1 nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1. In other embodiments, the nucleic acid is at least 30, 50, 100, 250 or 560 nucleotides in length. As used herein, the term "hybridizes under stringent conditions" is intended to describe conditions for hybridization and washing under which nucleotide sequences at least 76%, homologous to each other typically remain hybridized to each other. Preferably, the conditions are such that sequences at least about 80%, more preferably, at least about 85%, and even more preferably at least about 90% or more homologous to each other typically remain hybridized to each other. Such stringent conditions are known to those skilled in the art and can be found in *Current Protocols in Molecular Biology*, John Wiley & Sons, N. Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 corresponds to a naturally occurring nucleic acid molecule. As used herein a "naturally-occurring" nucleic acid molecule refers to an RNA or DNA molecule having nucleotide a sequence that occurs in nature (e.g., encodes a natural protein). In one embodiment, the nucleic acid encodes a natural human NPG-1.

In addition to naturally-occurring allelic variants of the NPG-1 sequence that may exist in the population, the skilled artisan will further appreciate that changes can be introduced by mutation into the nucleotide sequence of SEQ ID NO:1, thereby leading to changes in the amino acid sequence of the encoded NPG-1 protein, without altering the functional ability of the NPG-1 protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of NPG-1 (e.g., the sequence of SEQ ID NO:2) without altering the activity of NPG-1, whereas an "essential" amino acid residue is required for NPG-1 activity. For example, conserved amino acid residues, e.g., tryptophans and serines, in the type I thmmbospondin repeat domain of NPG-1 are most likely important for binding to extracellular matrix components and are thus essential residues of NPG-1. Other amino acid residues, however, (e.g., those that are not conserved or only semi-conserved in the type I thrombospondin repeat domain) may not be essential for activity and thus are likely to be amenable to alteration without altering NPG-1 activity.

Accordingly, another aspect of the invention pertains to nucleic acid molecules encoding NPG-1 proteins that contain changes in amino acid residues that are not essential for NPG-1 activity. Such NPG-1 proteins differ in amino acid sequence from SEQ ID NO:2 yet retain at least one of the NPG-1 activities described herein. In one embodiment the isolated nucleic acid molecule comprises a nucleotide sequence encoding a protein, wherein the protein comprises an amino acid sequence at least about 76%, 80%, 85%, 90%, 95%, or 98% or more homologous to SEQ ID NO:2. In another embodiment, the isolated nucleic acid encodes a protein which differs from the naturally occurring NPG-1 polypeptide (SEQ ID NO:2) by at least 5, 10, 20, 50, 100, 150 or 170 amino acids, but no more than 200 amino acids.

"Sequence identity or homology", as used herein, refers to the sequence similarity between two polypeptide molecules or between two nucleic acid molecules. To determine the percent homology of two amino acid sequences (e.g., SEQ ID NO:2) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions× 100). For example, if 6 of 10, of the positions in two sequences are matched or homologous then the two sequences are 60% homologous or have 60% sequence identity. By way of example, the DNA sequences ATTGCC and TATGGC share 50% homology or sequence identity. Generally, a comparison is made when two sequences are aligned to give maximum homology or sequence identity.

The comparison of sequences and determination of percent homology between two sequences can be accomplished using a mathematical algorithm. A preferred, non-limiting example of a mathematical algorithm utilized for the comparison of sequences is the algorithm of Karlin and Altschul *Proc. Natl. Acad. Sci.* USA 87:2264–68, 1990, modified as in Karlin and Altschul *Proc. Natl. Acad. Sci.* USA 90:5873–77, 1993. Such an algorithm is incorporated into the NBLAST and XBLAST programs (version 2.0) of Altschul, et al. *J. Mol. Biol.* 215:403–10, 1990. BLAST nucleotide searches can be performed with the NBLAST program, score=100, wordlength-12 to obtain nucleotide sequences homologous to NPG-1 nucleic acid molecules of the invention. BLAST protein searches can be performed with the XBLAST program, score=50, wordlength=3 to obtain amino acid sequences homologous to NPG-1 protein molecules of the invention. To obtain gapped alignments for comparison purposes. Gapped BLAST can be utilized as described in Altschul et al., *Nucleic Acids Res.* 25(17):3389–3402, 1997. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

An isolated nucleic acid molecule encoding an NPG-1 protein homologous to the protein of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in NPG-1 is preferably replaced with another amino acid residue from the same side chain family. Alternatively, in another embodiment mutations can be introduced randomly along all or part of an NPG-1 coding sequence, such as by saturation mutagenesis, and the resultant mutants can be screened for an NPG-1 activity described herein to identify mutants that retain NPG-1 activity. Following mutagenesis of SEQ ID NO:1, the encoded protein can be expressed recombinantly (e.g., as described in the Examples section) and the activity of the protein can be determined using, for example, assays described herein.

In addition to the nucleic acid molecules encoding NPG-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire NPG-1 coding strand, or to only a portion thereof. In one embodiment, an antisense nucleic acid molecule is antisense to a "coding region" of the coding strand of a nucleotide sequence encoding NPG-1. The term "coding region" refers to the region of the nucleotide sequence comprising codons which are translated into amino acid residues (e.g., the coding region of SEQ ID NO:1 comprises nucleotides 235 to 1225). In another embodiment, the antisense nucleic acid molecule is antisense to a "noncoding region" of the coding strand of a nucleotide sequence encoding NPG-1. The term "noncoding region" refers to 5' and 3' sequences which flank the coding region that are not translated into amino acids (i.e., also referred to as 5' and 3' untranslated regions).

Given the coding strand sequences encoding NPG-1 disclosed herein (e.g., SEQ ID NO:1), antisense nucleic acids of the invention can be designed according to the rules of Watson and Crick base pairing. The antisense nucleic acid molecule can be complementary to the entire coding region of NPG-1 mRNA, but more preferably is an oligonucleotide which is antisense to only a portion of the coding or noncoding region of NPG-1 mRNA. For example, the antisense oligonucleotide can be complementary to the region surrounding the translation start site of NPG-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethylthiouridine, 5-carboxymethyl-2-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid(v), wybutoxosine, pseudouracil, queosine, 2-thiocytosine, S-methylthiouracil, 2-thiouracil, 4-thiouracil, 5-methyluracil, uracil-5-oxyacetic acid methylester, uraciloxyacetic acid(v), 5-methylthiouracil, 3-(3-aminoNcarboxypropyl) uracil, (acp3) w, and 2,6-diaminopurine. Alternatively, the antisense nucleic acid can be produced biologically using an expression vector into which a nucleic acid has been subcloned in an antisense orientation (i, e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an NPG-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an a-anomeric nucleic acid molecule. An α-anomeric nucleic acid molecule forms specific double-stranded hybrids with complementary RNA in which, contrary to the usual B-units, the strands run parallel to each other (Gaultier et al. (1987) *Nucleic Acids. Res.* 15: 6625–6641). The antisense nucleic acid molecule can also comprise a 2% methylribonucleotide (Inoue et al. (1987) *Nucleic Acids Res.* 15: 613 1–6 148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead Ribozymes (described in Haselhoff and Gerlach (1988) *Nature* 334: 585–591)) can be used to catalytically cleave NPG-1 mRNA transcripts to thereby inhibit translation of NPG-1 mRNA. A Ribozymes having specificity for an NPG-1 encoding nucleic acid can be designed based upon the nucleotide sequence of an NPG-1 cDNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in an NPG-1 encoding mRNA. See, e.g., Cech et al. U.S. Pat. No. 4,987,071 and Cech et al. U.S. Pat. No. 5,116,742. Alternatively, NPG-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, NPG-1 gene expression can be inhibited by targeting nucleotide sequences complementary to the regulatory region of the NPG-1 (e.g., the NPG-1 promoter and/or enhancers) to form triple helical structures that prevent transcription of the NPG-1 gene in target cells. See generally, Helene, C. (1991) *Anticancer Drug Des.* 6(6): 569–84; Helene, C. et al. (1992) *Ann. N. Y. Acad. Sci.* 660:27–36; and Maher, L. J. (1992) *Bioassays* 14(12): 807–15.

III. Recombinant Expression Vectors and Host Cells

Another aspect of the invention pertains to vectors, preferably expression vectors, containing a nucleic acid encoding NPG-1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adenoassociated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression which is operatively linked to the nucleic acid sequence to be expressed. Within a recombinant expression vector, "operably linked" is intended to mean that. the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NPG-1 proteins, mutant forms of NPG-1, fusion proteins, etc.).

The recombinant expression vectors of the invention can be designed for expression of NPG-1 in prokaryotic or eukaryotic cells. For example, NPG-1 can be expressed in bacterial cells such as *E. coli*, insect cells (using baculovirus expression vectors) yeast cells or mammalian cells. Suitable host cells are discussed further in Goeddel, *Gene Expression Technology:Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein, 2) to increase the solubility of the recombinant protein, and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson K. S. (1988) *Gene* 67: 31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the NPG-1 is cloned into a pGEX expression vector to create a vector encoding a fusion protein comprising, from the N-terminus to the C-terminus, GST-thrombin cleavage site-19-NPG-1. The fusion protein can be purified by affinity chromatography using glutathione agarose resin. Recombinant NPG-1 unfused to GST can be recovered by cleavage of the fusion protein with thrombin.

Examples of suitable inducible non-fusion *E. coli* expression vectors include pTrc (Amann et al., (1988) *Gene* 69: 301–3 15) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 10-lac fusion promoter mediated by a coexpressed viral RNA polymerase (T7 gnl). This viral polymerase is supplied by host strains BL21 (DE3) or HMS 174 (DE3) from a resident λ prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20: 2111–2118). Such alteration of nucleic acid sequences of the invention can be carried out by standard DNA synthesis techniques.

In another embodiment, the NPG-1 expression vector is a yeast expression vector. Examples of vectors for expression in yeast *S. cerivisae* include pYepSec1 (Baldari, et al., (1987) *Embo J.* 6: 229–234), pMFa (Kurjan and Herskowitz, (1982) *Cell* 30: 933–943), pJRY88 (Schultz et al., (1987) *Gene* 54: 113–23), 1 and pYES2 (Invitrogen Corporation San Diego, Calif.).

Alternatively, NPG-1 can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3: 2156–2165) and the pVL series (Lucklow and Summers (1989) *Virology* 170: 3 1–39).

In yet another embodiment's nucleic acid of the invention is expressed in mammalian cells using a mammalian expression vector. Examples of mammalian expression vectors include pCDM8 (Seed, 8. (1987) *Nature* 329:840) and pMT2PC (Kaufinan et al. (1987) *EMBO J.* 6:187–1 95). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd ed, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally regulated promoters are also encompassed, for example the murine hox promoters (Kessel and Gruss (1990) *Science* 249:374–379) and the α-fetoprotein promoter (Campes and Tilghman (1989) *Genes Dev.* 3: 537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to NPG-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1 (1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term aa used herein. A host cell can be any prokaryotic or eukaryotic cell. For example, NPG-1 protein can be expressed in bacterial cells such as *E. coli*, insect cells, yeast or mammalian cells such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding NPG-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NPG-1 protein. Accordingly, the invention further provides methods for producing NPG-1 protein using the host cells of the invention. In one embodiment, the method comprises culturing the host cell of invention (into which a recombinant expression vector encoding NPG-1 has been introduced) in a suitable medium until NPG-1 is produced. In another embodiment, the method further comprises isolating NPG-1 from the medium or the host cell.

The host cells of the invention can also be used to produce nonhuman transgenic animals. The nonhuman transgenic animals can be used in screening assays designed to identify agents or compounds, e. g:, drugs, pharmaceuticals, etc., which are capable of ameliorating detrimental symptoms of selected disorders such as cardiovascular disorders and proliferative disorders. For example, in one embodiment, a host cell of the invention is a fertilized oocyte or an embryonic stem cell into which NPG-1 coding sequences have been introduced. Such host cells can then be used to create non-human transgenic animals in which exogenous NPG-1 sequences have been introduced into their genome or homologous recombinant animals in which endogenous NPG-1 sequences have been altered. Such animals are useful for studying the function and/or activity of NPG-1 and for identifying and/or evaluating modulators of NPG-1 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous NPG-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NPG-1-encoding nucleic acid into the male pronuclei of a fertilized oocyte, e.g., by microinjection, retroviral infection, and allowing the oocyte to develop in a pseudopregnant female foster animal. The human NPG-1 cDNA sequence of SEQ ID NO:1 can be introduced as a transgene into the genome of a nonhuman animal. Alternatively, a nonhuman homologue of the human NPG-1 gene, such as a mouse NPG-1 gene, can be isolated based on hybridization to the human NPG-1 cDNA (described further in subsection II above) and used as a transgene. Intronic sequences and polyadenylation signals can also be included in the transgene to increase the efficiency of expression of the transgene. A tissue-specific regulatory sequence(s) can be operably linked to the NPG-1 transgene to direct expression of NPG-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon ihe presence of the NPG-1 transgene in its genome and/or expression of NPG-1 mRNA in tissues or cells of the animals. A transgenic founder animal can then be used to breed additional animals carrying the tranggene. Moreover, transgenic animals carrying a transgene encoding NPG-1 can further be bred to other transgenic animals carrying other transgenes.

To create a homologous recombinant animal, a vector is prepared which contains at least a portion of an NPG-1 gene into which a deletion, addition or substitution has been introduced to thereby alter, e.g., functionally disrupt, the NPG-1 gene. The NPG-1 gene can be a human gene (e.g., from a human genomic clone isolated from a human genornic library screened with the cDNA of SEQ ID NO: 1), but more preferably, is a nonhuman homologue of a human NPG-1 gene. For example, a mouse NPG-1 gene can be isolated from a mouse genomic DNA library using the human NPG-1 cDNA of SEQ ID NO:1 as a probe. The mouse NPG-1 gene then can be used to construct a homologous recombination vector suitable for altering an endogenous NPG-1 gene in the mouse genome. In a preferred embodiment, the vector is designed such that, upon homologous recombination, the endogenous NPG-1 gene is functionally disrupted (i.e., no longer encodes a functional protein; also referred to as a "knock out" vector). Alternatively, the vector can be designed such that, upon homologous recombination, the endogenous NPG-1 gene is mutated or otherwise altered but still encodes functional protein (e.g., the upstream regulatory region can be altered to thereby alter the expression of the endogenous NPG-1 protein). In the homologous recombination vector, the altered portion of the NPG-1 gene is flanked at its 5' and 3' ends by additional nucleic acid of the NPG-1 gene to allow for homologous recombination to occur between the exogenous NPG-1 gene carried by the vector and an endogenous NPG-1 gene in an embryonic stem cell. The additional flanking NPG-1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced NPG-1 gene has homologously recombined with the endogenous NPG-1 gene are selected (see e.g., Li, E. et al. (1992) *Cell* 69: 915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in biotechnology 2: 823–829 and in PCT International Publication Nos.: WO 90/11354 by Le Mouellec et al.; WO 91101140 by Smithies et al.; WO 92/0968 by Zijlstra et al.; and WO 93104 169 by Berns et al.

In another embodiment, transgenic nonhumans animals can be produced which contain selected systems which allow for regulated expression of the transgene. One example of such a system is the cre/loxP recombinase system of bacteriophage P1. For a description of the cre/ZoxP recombinase system, see, e.g., Lakso et al. (1992) PNAS 89: 6232–6236. Another example of a recombinase system is the FLP recombinase system of *Succharomyces cerevisiue* (O'Goman et al. (1991) *Science* 251: 1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) Nature 385: 810–813 and PCT International Publication Nos. WO 97/07668 and WO 97107669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

IV. Isolated NPG-1 Proteins and Anti-NPG-1 Antibodies

Another aspect of the invention pertains to isolated NPC-1 proteins, and biologically active portions thereof, as well as peptide fragments suitable for use as immunogens to raise anti-NPG-1 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of NPG-1 protein in which the protein is separated from cellular components of the cells in which it is naturally or recombinantly produced. In one embodiment, the language "substantially free of cellular material" includes preparations of NPG-1 protein having less than about 30% (by dry weight) of non-NPG-1 protein (also referred to herein as a "contaminating protein"), more preferably less than about 20% of non-NPG-1 protein, still more preferably less than about 10% of non-NPG-1 protein, and most preferably less than about 5% non-NPG-1 protein. When the NPG-1 protein or biologically active portion thereof is recombinantly produced it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of NPG-1 protein in which the protein is separated from chemical precursors or other chemicals which are involved in the synthesis of the protein. In one embodiment, the language "substantially free of chemical precursors or other chemicals" includes preparations of NPG-1 protein having less than about 30% (by dry weight) of chemical precursors or non-NPG-1 chemicals, more preferably less than about 20% chemical precursors or non-NPG-1 chemicals, still more preferably less than about 10% chemical precursors or non-NPG-1 chemicals, and most preferably less than about 5% chemical precursors or non-NPG-1 chemicals. In preferred embodiments, isolated proteins or biologically active portions thereof lack contaminating proteins from the same animal from which the NPG-1 protein is derived. Typically, such proteins are produced by recombinant expression of, for example, a human NPG-1 protein in a nonhuman cell.

An isolated NPG-1 protein or a portion thereof of the invention can modulate tumor cell adhesion, e.g., malignant prostate cell adhesion. In preferred embodiments, the protein or portion thereof comprises an amino acid sequence which is sufficiently homologous to an amino acid sequence of SEQ ID NO:2 such that the protein or portion thereof maintains the ability to modulate tumor cell adhesion, e.g., malignant prostate cell adhesion. The portion of the protein is preferably a biologically active portion as described herein. In another preferred embodiment, the NPG-1 protein (i.e., amino acid residues 1–330) has an amino acid sequence shown in SEQ ID NO:2. The preferred NPG-1 proteins of the present invention also preferably possess at least one of the NPG-1 activities described herein.

In other embodiments, the NPG-1 protein is substantially homologous to the amino acid sequence of SEQ ID NO:2 and retains the functional activity of the protein of SEQ ID NO:2 yet differs in amino acid sequence due to natural allelic variation or mutagenesis, as described in detail in subsection I above. Accordingly, in another embodiment, the NPG-1 protein is a protein which comprises an amino acid sequence which is at least about 76%, 80%, 85%, 90%, 95%, or 98% or more homologous to the entire amino acid sequence of SEQ ID NO:2 and which has at least one of the NPG-1 activities described herein. In another embodiment, the invention pertains to a fill length human protein which is substantially homologous to the entire amino acid sequence of SEQ ID NO:2.

Biologically active portions of the NPG-1 protein include peptides comprising amino acid sequences derived from the amino acid sequence of the NPG-1 protein, e.g., the amino acid sequence shown in SEQ ID NO:2 or the amino acid sequence of a protein homologous to the NPG-1 protein which include less amino acids than the full length NPG-1 protein or the full length protein which is homologous to the NPG-1 protein and exhibit at least one activity of the NPG-1 protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a type I thrombospondin repeat domain with at least one activity of the NPG-1 protein. Preferably, the domain is a type I thrombospondin repeat domain derived from a human and is at least about 76%, 80%, 85%, 90% 95%, or 98% or more homologous to SEQ ID NO:3. In a preferred embodiment, the biologically active portion of the protein which includes the type I thrombospondin repeat domain can modulate cell adhesion in a tumor cell, e.g., a malignant prostate cell, to thereby beneficially affect the tumor cell. In a preferred embodiment, the biologically active portion comprises the type I thrombospondin repeat domain of NPG-1 as represented by amino acid residues 258 to 294 of SEQ ID NO:2 and shown separately as SEQ ID NO:3. Moreover, other biologically active portions, in which other regions of the protein are deleted can be prepared by recombinant techniques and evaluated for one or more of the activities described herein. Preferably, the biologically active portions of the NPG-1 protein include one or more selected domains/motifs or portions thereof having biological activity.

NPG-1 proteins are preferably produced by recombinant DNA techniques. For example, a nucleic acid molecule encoding the protein is cloned into an expression vector (as described above), the expression vector is introduced into a host cell (as described above) and the NPG-1 protein is expressed in the host cell. The NPG-1 protein can then be isolated from the cells by an appropriate purification scheme using standard protein purification techniques. Alternative to recombinant expression, an NPG-1 protein, polypeptide, or peptide can be synthesized chemically using standard peptide synthesis techniques. Moreover, native NPG-1 protein can be isolated from ncells (e.g., prostate cells), for example, using an anti-NPG-1 antibody (described further below).

The invention also provides NPG-1 chimeric or fusion proteins. As used herein, an NPG-1 "chimeric protein" or "fusion protein" comprises an NPG-1 polypeptide operatively linked to a non-NPG-1 polypeptide. An "NPG-1 polypeptide" refers to a polypeptide having an amino acid sequence corresponding to NPG-1, whereas a "non-NPG-1 polypeptide" refers to a polypeptide having an amino acid sequence corresponding to a protein which is not substantially homologous to the NPG-1 protein, e.g., a protein which is different from the NPG-1 protein and which is derived from the same or a different organism. Within the fusion protein, the term "operatively linked" is intended to indicate that the NPG-1 polypeptide and the non-NPG-1 polypeptide are fused in-frame to each other. The non-NPG-1 polypeptide can be fused to the N-terminus or C-terminus of the NPG-1 polypeptide. For example, in one embodiment the fusion protein is a GST-NPG-1 fusion protein in which the NPG-1 sequences are fused to the C-terminus of the GST sequences. Such fusion proteins can facilitate the purification of recombinant NPG-1. In another embodiment, the fusion protein is an NPG-1 protein containing a heterologous signal sequence at its N-terminus. In certain host cells (e.g., mammalian host cells), expression and/or secretion of NPG-1 can be increased through use of a heterologous signal sequence.

Preferably, an NPG-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An NPG-1 encoding nucleic acid can be cloned into such an expression vector such that the fusion moiety is linked in-frame to the NPG-1 protein.

The present invention also pertains to homologues of the NPG-1 proteins which function as either an NPG-1 agonist (mimetic) or an NPG-1 antagonist. In a preferred embodiment, the NPG-1 agonists and antagonists stimulate or inhibit, respectively, a subset of the biological activities of the naturally occurring form of the NPG-1 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the NPG-1 protein.

Homologues of the NPG-1 protein can be generated by mutagenesis, e.g., discrete, point mutation or truncation of the NPG-1 protein. As used herein, the term "homologue" refers to a variant form of the NPG-1 protein which acts as an agonist or antagonist of the activity of the NPG-1 protein. An agonist of the NPG-1 protein can retain substantially the same, or a subset, of the biological activities of the NPG-1 protein. An antagonist of the NPG-1 protein can inhibit one or more of the activities of the naturally occurring form of the NPG-1 protein, by, for example, competitively binding to a downstream or upstream member of the NPG-1 cascade which includes the NPG-1 protein. Thus, the mammalian NPG-1 protein and homologues thereof of the present invention can be either positive or negative regulators of cell adhesion in tumor cells, e.g., malignant prostate cells.

In an alternative embodiment, homologues of the NPG-1 protein can be identified by screening combinatorial libraries of mutants, e.g., truncation mutants, of the NPG-1 protein for NPG-1 protein agonist or antagonist activity. In one embodiment, a variegated library of NPG-1 variants is generated by combinatorial mutagenesis at the nucleic acid level and is encoded by a variegated gene library. A variegated library of NPG-1 variants can be produced by, for example, enzymatically ligating a mixture of synthetic oligonucleotides into gene sequences such that a degenerate set of potential NPG-1 sequences is expressible as individual polypeptides, or alternatively, as a set of larger fusion proteins (e.g., for phage display) containing the set of NPG-1 sequences therein. There are a variety of methods which can be used to produce libraries of potential NPG-1 homologues from a degenerate oligonucleotide sequence. Chemical synthesis of a degenerate gene sequence can be performed in an automatic DNA synthesizer, and the synthetic gene then ligated into an appropriate expression vector. Use of, a degenerate set of genes allows for the provision, in one mixture, of all of the sequences encoding the desired set of potential NPG-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; et al. (1983) *Nucleic AcidRes.* 11:477.

In addition, libraries of fragments of the NPG-1 protein coding can be used to generate a variegated population of NPG-1 fragments for screening and subsequent selection of homologues of an NPG-1 protein. In one embodiment, a library of coding sequence fragments can be generated by treating a double stranded PCR fragment of an NPG-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the NPG-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NPG-1 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected: Recursive ensemble mutagenesis (REM), a new technique which enhances the frequency of functional mutants in the libraries, can be used in combination with the screening assays to identify NPG-1 homologues (Arkin and Your-van (1992) *PNAS* 89: 7811–7815; Delgrave et al. (1993) *Protein Engineering* 6(3):327–331).

In one embodiment, cell based assays can be exploited to analyze a variegated NPG-1 library. For example, a library of expression vectors can be transfected into a tumor cell, e.g., a benign or malignant prostate cell line. The transfected cells are then allowed to grow and the effect of the NPG-1 mutant on cell migration can be detected, e.g., by measuring cell migration using a Boyden chamber invasion assay. Plasmid DNA can then be recovered from the cells which score for inhibition of cell invasion, and the individual clones further characterized.

An isolated NPG-1 protein, or a portion or fragment thereof, can be used as an immnunogen to generate antibodies that bind NPG-1 using standard techniques for polyclonal and monoclonal antibody preparation. The fill-length NPG-1 protein can be used or, alternatively, the invention provides antigenic peptide fragments of NPG-1 for use as imunogens. The antigenic peptide of NPG-1 comprises at least 8 amino acid residues of the amino acid sequence shown in SEQ ID NO:2 and encompasses an epitope of NPG-1 such that an antibody raised against the peptide forms a specific immune complex with NPG-1. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of NPG-1 that are located on the surface of the protein, e.g., hydrophilic regions. An NPG-1 immunogen typically is used to prepare antibodies by immunizing a suitable subject, (e.g., rabbit, goat, mouse or other mammal) with the immunogen. An appropriate immunogenic preparation can contain, for example, recombinantly expressed NPG-1 protein or a chemically synthesized NPG-1 peptide. The preparation can further include an adjuvant, such as Freund's complete or incomplete adjuvant, or similar immunostimulatory agent. Immunization of a suitable subject with an immunogenic NPG-1 preparation induces a polyclonal anti-NPG-1 antibody response.

Accordingly, another aspect of the invention pertains to anti-NPG-1 antibodies,. The term "antibody" as used herein refers to immunoglobulin molecules and immunologically active portions of immunoglobulin molecules, i.e., molecules that contain an antigen binding site which specifically binds (immunoreacts with) an antigen, such as NPG-1. Examples of immunologically active portions of immunoglobulin molecules include F (ab) and F (ab') z fragments which can be generated by treating the antibody with an enzyme such as pepsin. The invention provides polyclonal and monoclonal antibodies that bind NPG-1. The term "monoclonal antibody" or "monoclonal antibody composition", as used herein, refers to a population of antibody molecules that contain only one species of an antigen binding site capable of immunoreacting with a particular epitope of NPG-1. A monoclonal antibody composition thus typically displays a single binding affinity for a particular NPG-1 protein with which it imrnunoreacts.

Polyclonal anti-NPG-1 antibodies can be prepared as described above by immunizing a suitable subject with an NPG-1 immunogen. The anti-NPG-1 antibody titer in the immunized subject can be monitored over time by standard techniques, such as with an enzyme linked immunosorbent assay (ELISA) using immobilized NPG-1. If desired, the antibody molecules directed against NPG-1 can be isolated from the mammal (e.g., from the blood) and further purified by well-known techniques, such as protein A chromatography to obtain the IgG fraction. At an appropriate time after immunization, e.g., when the anti-NPG-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127: 539–46; Brown et al. (1980) *J. Biol. Chem* .255:4980–83; Yeh et al. (1976) PNAS 76: 2927–3 1; and Yeh et al. (1982) *Int. J Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R Liss, Inc., pp.77–96) or triorna techniques. The technology for producing monoclonal antibody hybridomas is well known (see generally R H. Kenneth, in *Monoclonal Antibodies: A New Dimension in Biological Analyses*, Plenum Publishing, Corp., New York, N.Y. (1980); E. A. Lerner (1981) *Yale J. Biol. Med.* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an NPG-1 immunogen as described above, and the culture supernatants of the resulting hybridoma cells are screened to identify a hybridoma producing a monoclonal antibody that binds NPG-1.

Any of the many well known protocols used for fusing lymphocytes and immortalized cell lines can be applied for the purpose of generating an anti-NGP-1 monoclonal antibody (see, e.g., G. Galfre et al. (1977) *Nature* 266:55052; Gefter et al. *Somatic Cell Genet.*, cited supra; Lerner, Yale J. Biol. Med., cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NPG-1, e.g., using a standard ELISA assay.

Alternative to preparing monoclonal antibody-secreting hybridomas, a monoclonal anti-NPG-1 antibody can be identified and isolated by screening a recombinant combinatorial immunoglobulin library (e.g., an antibody phage display library) with NPG-1 to thereby isolate immunoglobulin library members that bind NPG-1. Kits for generating and screening phage display libraries are commercially available (e.g., the Pharmacia *Recombinant Phage Antibody System*, Catalog No. 27-9400-01; and the Stratagene SurZAP™ Phage Display Kit, Catalog No. 240612).

Additionally, examples of methods and reagents particularly amendable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication No. WO 92/20791; Markland et al. PCT International Publication No. WO 92/15679; Breitling et al. PCT International Publication No. WO 92/01047; Garrard et al. PCT International Publication No. WO 92/09690; Ladner et al. PCT International Publication No. WO 90/02809; Fuchs et al. (1991) *Bio/technology* 9: 1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Biotechnology* 9:1373–1377; Hoogenboom et al. (1991) *Nuc. Acid Res.* 19: 4133–4137; Barbas et al. (1991) *PNAS* 88:7978–7982; and McCafTerty et al. *Nature* (1990) 348:552–554.

Additionally, recombinant anti-NPG-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184, 187; Taniguchi, M., European Patent Application 171, 496; Morrison et al. European Patent Application 173, 494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Cunc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-NPG-1 antibody (e.g., monoclonal antibody) can be used to isolate NPG-1 by standard techniques, such as affinity chromatography or immunoprecipitation. An anti-NPG-1 antibody can facilitate the purification of natural NPG-1 from cells and of recombinantly produced NPG-1 expressed in host cells. Moreover, an anti-NPG-1 antibody can be used to detect NPG-1 protein (e.g., in a cellular lysate or cell supematant) in order to evaluate the abundance and pattern of expression of the NPG-1 protein. Anti-NPG-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, B-galactosidase, or acetylcholinesterase; examples of suitable prosthetic group complexes include strepavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

V. Pharmaceutical Compositions

The NPG-1 nucleic acid molecules, NPG-1 proteins, NPG-1 modulators, and antiNPG-1 antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; annoxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an NPG-1 protein or anti-NPG-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin, an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack or dispenser together with instructions for administration.

VI. Uses and Methods of the Invention

The nucleic acid molecules, proteins, protein homologues, and antibodies described herein can be used in one or more of the following methods: a) screening assays; b) detecting assays (e.g., chromosome mapping, tissue typing, and forensic biology); C) predictive medicine (e.g., diagnostic assays, prognostic assays, monitoring clinical trials, and pharmacogenetics); and d) methods of treatment (e.g., therapeutic and prophylactic methods as well as such methods in the context of pharmacogenomics). As described herein, an NPG-1 protein of the invention has one or more of the following activities: 1) it can bind to the extracellular matrix, e.g., the basal lamina; 2) it can interact with a growth factor, e.g., VEGF; 3) it can interact with a cytokine; 4) it can modulate tumor cell adhesion; 5) it can modulate tumor cell invasion; 6) it can modulate tumor cell migration; 7) it can modulate tumor metastasis; 8) it can modulate tumor angiogenesis; 9) it can modulate extracellular matrix degradation, e.g., via tumor secreted proteases; 10) it can modulate cell proliferation 11) it can modulate tissue architecture and differentiation, e.g., cellular architecture and differentiation; 12) it can modulate adhesion and outgrowth of embryonic neurons; 13) it can modulate the attachment of neurons; 14) it can modulate, e.g., stimulate, the growth of nerve cells; and 15) it can modulate the regeneration nerve cell growth.

The NPG-1 proteins of the invention can thus be used in, for example: 1) modulation of binding to the extracellular matrix, e.g., the basal lamina; 2) modulation of tumor cell adhesion; 3) modulation of tumor cell-invasion; 4) modulation of tumor cell migration; 5) modulation of tumor cell metastasis; 6) modulation of tumor cell angiogenesis; 7) modulation, of extracellular matrix degradation, e.g., via tumor secreted proteases; and 8) modulation of tissue architecture and differentiation, e.g., cellular architecture and differentiation.

The isolated nucleic acid molecules of the invention can be used, for example, to express an NPG-1 protein (e.g., via a recombinant expression vector in a host cell in gene therapy applications), to detect NPG-1 mRNA (e.g., in a biological sample) or a genetic alteration in an NPG-1 gene, and to modulate NPG-1 activity, as described further below. In addition, the NPG-1 proteins can be used to screen drugs or compounds which modulate the NPG-1 activity as well as to treat disorders characterized by insufficient or excessive production of NPG-1 protein or production of NPG-1 protein forms which have decreased or aberrant activity compared to NPG-1 wild type protein (e.g., proliferative diseases such as cancer). Moreover, the anti-NPG-1 antibodies of the invention can be used to detect and isolate NPG-1 proteins, regulate the bioavailability of NPG-1 proteins, and modulate NPG-1 activity.

A. Screening Assays

The invention provides a method (also referred to herein as a "screening assay") for identifying modulators, i.e., candidate or test compounds or agents (e.g., peptides, peptidomimetics, small molecules or other drugs) which bind to NPG-1 proteins or have a stimulatory or inhibitory effect on, for example, NPG-1 expression or NPG-1 activity.

In one embodiment, the invention provides assays for screening candidate or test compounds which bind to or modulate the activity of an NPG-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer *Drug Des.* 12:145).

Examples of methods for the synthesis of molecular libraries can be found in the art, for example in: Dewitt et al. (1993) *Proc. Natl. Acad Sci. U.S.A.* 906909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. EngZ.* 33:2059; Carell et al. (1994) *Angew. Chem. Int. Ed. Engl.* 33:2061; and in Gallop et al. (1994) *J Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad Sci.* 87:6378–6382); (Felici(1991) *J. Mol. Biol.* 222:301–310); (Ladner supra.).

In one embodiment, an assay is a cell-based assay in which a cell which expresses NPG-1, e.g., a human prostate cancer cell line LNCaP, is contacted with a test compound and the ability of the test compound to modulate an NPG-1 activity is determined. The cell, for example, can be of mammalian origin or a yeast cell. Determining the ability of the test compound to modulate an NPG-1 activity can be accomplished by methods known in the art as described in, for example, Tuszynsk, G. P. et al. (1987) *Science* 236:1570–1573, Taraboletti, G. et al. (1987) *J Cell Biol.* 105:2409–2415, and Castle, V. et al. (1991) *J. Clin. Invest.* 87:1883–1888. More specifically, the ability of the test compound to modulate tumor cell motility can be determined using the Boyden chamber cell motility assay (Taraboletti et al. (1987)).

Cell adhesion and invasion can be determined by the use of fibrin gels as described in, for example, Hosokawa, T. et al. (1993) *Oncology Res.* 5:183–189. Moreover, tumor growth kinetics can be determined using the assays described in, for example, Horoszewicz, J. S. et al. (1983) *Cancer Res.* 43:1809–1818.

The ability of the test compound to bind to NPG-1 may also be determined by coupling the test compound with a radioisotope or enzymatic label such that binding of the test compound to NPG-1 can be determined by detecting the labeled compound in a complex. For example, test compounds can be labeled with $^{125}I$, $^{36}S$, $^{14}C$ or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with NPG-1 without the labeling of any of the interactants. For example, a microphysiometer can be used to detect the interaction of a test compound with NPG-1 without the labeling of either the test compound or NPG-1. McConnell, H. M. et al. (1992) *Science* 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and receptor.

In yet another embodiment, an assay of the present invention is a cell-free assay in which an NPG-1 protein or biologically active portion thereof is contacted with a test compound and the ability of the test compound to bind to the NPG-1 protein or biologically active portion thereof is determined. Binding of the test compound to the NPG-1 protein can be determined either directly or indirectly as described above. In a preferred embodiment, the assay includes contacting the NPG-1 protein or biologically active portion thereof with a known compound which binds NPG-1 to form an assay mixture, contacting the assay mixture with a test compound, and determining the ability of the test compound to interact with an NPG-1 protein, wherein determining the ability of the test compound to interact with an NPG-1 protein comprises determining the ability of the test compound to preferentially bind to NPG-1 or biologically active portion thereof as compared to the known compound.

In another embodiment, the assay is a cell-free assay in which an NPG-1 protein or biologically active portion thereof is contacted with a test compound and the ability of the test compound to modulate (e.g., stimulate or inhibit) the activity of the NPG-1 protein or biologically active portion thereof is determined. Determining the ability of the test compound to modulate the activity of an NPG-1 protein can be accomplished, for example, by determining the ability of the NPG-1 protein to bind to an NPG-1 target molecule by one of the methods described above for determining direct binding. Determining the ability of the NPG-1 protein to bind to an NPG-1 target molecule can also be accomplished using a technology such as real-time Bimolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another embodiment, the cell-free assay involves contacting an NPG-1 protein or biologically active portion thereof with a known compound which binds the NPG-1 protein to form an assay mixture, contacting the assay mixture with a test compound, and determining the ability of the test compound to interact with the NPG-1 protein, wherein determining the ability of the test compound to interact with the NPG-1 protein comprises determining the ability of the NPG-1 protein to preferentially bind to or modulate the activity of an NPG-1 target molecule.

The cell-free assays of the present invention are amenable to use of both soluble and/or membrane-bound forms of isolated proteins (e.g., NPG-1 proteins or biologically active portions thereof or NPG-1 target molecules). In the case of cell-free assays in which a membrane-bound form an isolated protein is used (e.g., a NPG-1 target molecule) it may be desirable to utilize a solubilizing agent such that the membrane-bound form of the isolated protein is maintained in solution. Examples of such solubilizing agents include non-ionic detergents such as n-octylgucoside, n-dodecylglucoside, n-dodecylmaltoside, octanoyl-N-methylglucamide, decanoyl-N-methylglucamide, Triton® X-100, Triton® X-114, Thesite®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]hydroxy-1-propane sulfonate (CHAPSO), or N-dodecyl=N, N-dimethylammonio-1-propane sulfonate.

In more than one embodiment of the above assay methods of the present invention, it may be desirable to immobilize either NPG-1 or its target molecule to facilitate separation of complexed from uncomplexed forms of one or both of the proteins, as well as to accommodate automation of the assay. Binding of a test compound to an NPG-1 protein, or interaction of an NPG-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/NPG-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or NPG-1 protein, and the mixture incubated under conditions conducive to complex formation (e.g., at physiological conditions for salt and PI-I). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NPG-1 binding or activity determined using standard techniques.

Other techniques for immobilizing proteins on matrices can also be used in the screening assays of the invention. For example, either an NPG-1 protein or an NPG-1 target, molecule can be immobilized utilizing conjugation of biotin and streptavidin. Biotinylated NPG-1 protein or target molecules can be prepared from biotin-NHS (N-hydroxysuccinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with NPG-1 protein or target molecules but which do not interfere with binding of the NPG-1 protein to its target molecule can be derivatized to the wells of the plate, and unbound target or NPG-1 protein trapped in the wells by antibody conjugation. Methods for detecting such complexes, in addition to those described above for the GST-immobilized complexes, include immunodetection of complexes using antibodies reactive with the NPG-1 protein or target molecule, as well as enzyme-linked assays which rely on detecting an enzymatic activity associated with the NPG-1 protein or target molecule.

In another embodiment, modulators of NPG-1 expression are identified in a method wherein a cell is contacted with a candidate compound and the expression of NPG-1 mRNA or protein in the cell is determined. The level of expression of NPG-1 mRNA or protein in the presence of the candidate compound is compared to the level of expression of NPG-1 mRNA or protein in the absence of the candidate compound. The candidate compound can then be identified as a modulator of NPG-1 expression based on this comparison. For example, when expression of NPG-1 mRNA or protein is greater (statistically significantly greater) in the presence of the candidate compound than in its absence, the candidate compound is identified as a stimulator of NPG-1 mRNA or protein expression. Alternatively, when expression of NPG-1 mRNA or protein is less (statistically significantly less) in the presence of the candidate compound than in its absence, the candidate compound is identified as an inhibitor of NPG-1 mRNA or protein expression. The level of NPG-1 mRNA or protein expression in the cells can be determined by methods described herein for detecting NPG-1 mRNA or protein.

In yet another aspect of the invention, the NPG-1 proteins can be used as "bait proteins" in a two: hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with NPG-1 ("NPG-1-binding proteins" or "NPG-1-bp") and modulate NPG-1 activity. Such NPG-1-binding proteins are also likely to be involved in the process by which an NPG-1 protein mediates cell adhesion.

The two-hybrid system is based on the modular nature of most transcription factors, which consist of separable DNA-binding and activation domains. Briefly, the assay utilizes two different DNA constructs. In one construct, the gene that codes for an NPG-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an NPG-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the NPG-1 protein.

This invention further pertains to novel agents identified by the above-described screening assays. Accordingly, it is within the scope of this invention to further use an agent identified as described herein in an appropriate animal model. For example, an agent identified as described herein (e.g., an NPG-1 modulating agent, an antisense NPG-1 nucleic acid molecule, an NPG-1 specific antibody, or an NPG-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the NPG-1 nucleotide sequences, described herein, can be used to map the location of the NPG-1 genes on a chromosome. The mapping of the NPG-1 sequences to chromosomes is an important first step in correlating these sequences with genes associated with disease.

Briefly, NPG-1 genes can be mapped to chromosomes by preparing PCR primers (preferably 15–25 bp in length) from the NPG-1 nucleotide sequences. Computer analysis of the NPG-1 sequences can be used to predict primers that do not span more than one exon in the genomic DNA, thus complicating the amplification process. These primers can then be –41-used for PCR screening of somatic cell hybrids containing individual human chromosomes. Only those hybrids containing the human gene corresponding to the NPG-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NPG-1 nucleotide sequences to design oligonucleotide primers, sublocalization can be achieved with panels of fragments from specific chromosomes. Other mapping strategies which can similarly be used to map an NPG-1 sequence to its chromosome include in situ hybridization (described in Fan, Y. et al. (1990) *PNAS*, 87:6223–27), pie-screening with labeled flow-sorted chromosomes, and preselection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can he identified individually. The FISH technique can be used with a DNA sequence as short as 500 or 600 bases. However, clones larger than 1, 000 bases have a higher likelihood of binding to a unique chromosomal location with sufficient signal intensity for simple detection. Preferably 1, 000 bases, and more preferably 2, 000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing be chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available online through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the NPG-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The NPG-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the NPG-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The NPG-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The coding and noncoding sequences of SEQ ID NO:1 can comfortably provide positive individual identification with a panel of approximately 10–2,000 primers which each yield a noncoding amplified sequence of 100 bases.

If a panel of reagents from NPG-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial NPG-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i. e. another DNA sequence that is unique to a particular individual). As mentioned above, actual base sequence information can be used for identification as an accurate alternative to patterns formed by restriction, enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the NPG-1 nucleotide sequences or portions thereof, e.g., fragments derived from all or part of the noncoding regions of SEQ ID NO:1, having a length of at least 20 bases, preferably at least 30 bases.

The NPG-1 nucleotide sequences described herein can further be used to provide polynucleotide reagents, e.g., labeled or labelable probes which can be used in, for example, an in situ hybridization technique, to identify a specific tissue, e.g., brain or lung tissue. This can be very useful in cases where a forensic pathologist is presented with a tissue of unknown origin. Panels of such NPG-1 probes can be used to identify tissue by species and/or by organ type.

In a similar fashion, these reagents, e.g., NPG-1 primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trails are used for prognostic (predictive) purposes to thereby treat an individual prophylactically. Accordingly, one aspect of the present invention relates to diagnostic assays for determining NPG-1 protein and/or nucleic acid expression as well as NPG-1 activity, in the context of a biological sample (e.g., blood, serum, cells, tissue) to thereby determine whether an individual is afflicted with a disease or disorder, or is at risk of developing a disorder, associated with aberrant NPG-1 expression or activity. The invention also provides for prognostic (or predictive) assays for determining whether an individual is at risk of developing a disorder associated with NPG-1 protein, nucleic acid expression or activity. For example, mutations in an NPG-1 gene can be assayed in a biological sample. Such assays can be used for prognostic or predictive purpose to thereby prophylactically treat an individual prior to the onset of a disorder characterized by or associated with NPG-1 protein, nucleic acid expression or activity.

Another aspect of the invention pertains to monitoring the influence of agents (e.g., drugs, compounds) on the expression or activity of NPG-1 in clinical trials.

These and other agents are described in further detail in the following sections.

1. Diagnostic Assays

An exemplary method for detecting the presence or absence of NPG-1 protein or nucleic acid in a biological sample involves obtaining a biological sample from a test subject and contacting the biological sample with a compound or an agent capable of detecting NPG-1 protein or nucleic acid (e.g., mRNA, genomic DNA) that encodes NPG-1 protein such that the presence of NPG-1 protein or nucleic acid is detected in the biological sample. A preferred agent for detecting NPG-1 mRNA or genomic DNA is a labeled nucleic acid probe capable of hybridizing to NPG-1 mRNA or genomic DNA. The nucleic acid probe can be, for example, a full-length NPG-1 nucleic acid, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to NPG-1 mRNA or genomic DNA. Other suitable probes for use in the diagnostic assays of the invention are described herein.

A preferred agent for detecting NPG-1 protein is an antibody capable of binding to NPG-1 protein, preferably an antibody with a detectable label. Antibodies can be polyclonal, or more preferably, monoclonal. An intact antibody, or a fragment thereof (e.g., Fab or F(ab') 2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect NPG-1 mRNA, protein, or genomic DNA in a biological sample in vitro as well as in vivo. For example, in vitro techniques for detection of NPG-1 mRNA include Northern hybridizations and in situ hybridizations. In vitro techniques for detection of NPG-1 protein include enzyme linked immunosorbent assays (ELISAs), Western blots, immunoprecipitations and immunofluorescence. In vitro techniques for detection of NPG-1 genomic DNA include Southern hybridizations. Furthermore, in vivo techniques for detection of NPG-1 protein include introducing into a subject a labeled anti-NPG-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting NPG-1 protein, mRNA, or genomic DNA, such that the presence of NPG-1 protein, mRNA or genomic DNA is detected in the biological sample, and comparing the presence of NPG-1 protein, mRNA or genomic DNA in the control sample with the presence of NPG-1 protein, mRNA or genomic DNA in the test sample.

The invention also encompasses kits for detecting the presence of NPG-1 in a biological sample. For example, the kit can comprise a labeled compound or agent capable of detecting NPG-1 protein or mRNA in a biological sample; means for determining the amount of NPG-1 in the sample; and means for comparing the amount of NPG-1 in the sample with a standard. The compound or agent can be packaged in a suitable container. The kit can further comprise instructions for using the kit to detect NPG-1 protein or nucleic acid.

2. Prognostic Assays

The diagnostic methods described herein can furthermore be utilized to identify subjects having or at risk of developing a disease or disorder associated with aberrant NPG-1 expression or activity. For example, the assays described herein, such as the preceding diagnostic assays or the following assays, can be utilized to identify a subject having or at risk of developing a disorder associated with NPG-1 protein, nucleic acid expression or activity such as a proliferative disorder, e.g., prostate cancer. Alternatively, the prognostic assays can be utilized to identify a subject having or at risk for developing a proliferative disease (e.g., prostate cancer). Thus, the present invention provides a method for identifying a disease or disorder associated with aberrant NPG-1 expression or activity in which a test sample is obtained from a subject and NPG-1 protein or nucleic acid (e. g, mRNA, genomic DNA) is detected, wherein the presence of NPG-1 protein or nucleic acid is diagnostic for a subject having or at risk of developing a disease or disorder associated with aberrant NPG-1 expression or activity. As used herein, a "test sample" refers to a biological sample obtained from a subject of interest. For example, a test sample can be a biological fluid (e.g., serum), cell sample, or tissue, e.g., prostate tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NPG-1 expression or activity. For example, such methods can be used to determine whether a subject can be effectively treated with an agent for a disorder, such as a proliferative disorder, e.g., prostate cancer. Alternatively, such methods can be used to determine whether a subject can be effectively treated with an agent for a proliferative disease (e.g., prostate cancer). Thus, the present invention provides methods for determining whether a subject can be effectively treated with an agent for a disorder associated with aberrant NPG-1 expression or activity in which a test sample is obtained and NPG-1 protein or nucleic acid expression or activity is detected (e.g., wherein the abundance of NPG-1 protein or nucleic acid expression or activity is diagnostic for a subject that can be administered the agent to treat a disorder associated with aberrant NPG-1 expression or/activity).

The methods of the invention can also be used to detect genetic alterations in an NPG-1 gene, thereby determining if a subject with the altered gene is at risk for a disorder characterized by aberrant development, aberrant cellular differentiation, or aberrant cellular proliferation. In preferred embodiments, the methods include detecting, in a sample of cells from the subject, the presence or absence of a genetic alteration, for example, an alteration affecting the integrity of a gene encoding an NPG-1-protein, or the mis-expression of the NPG-1 gene. For example, such genetic alterations can be detected by ascertaining the existence of at least one of: 1) a deletion of one or more nucleotides from an NPG-1 gene; 2) an addition of one or more nucleotides to an NPG-1 gene; 3) a substitution of one or more nucleotides of an NPG-1 gene, 4) a chromosomal rearrangement of an NPG-1 gene; 5) an alteration in the level of a messenger RNA transcript of an NPG-1 gene, 6) aberrant modification of an NPG-1 gene, such as of the methylation pattern of the genomic DNA, 7) the presence of a non-wild type splicing pattern of a messenger RNA transcript of an NPG-1 gene, 8) a non-wild type level of an NPG-1-protein, 9) allelic loss of an NPG-1 gene, and 10) inappropriate post-translational modification of an NPG-1-protein. As described herein, there are a large number of assays known in the art which can be used for detecting alterations in an NPG-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683, 202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the NPG-1-gene (see Abravaya et al. (1995) *Nucleic Acids Res* .23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an NPG-1 gene under conditions such that hybridization and amplification of the NPG-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, *Proc. Natl. Acad. Sci. USA* 87:1874–1878), transcriptional amplification system (Kwoh, D. Y. et al., 1989, *Proc. Natl. Acad. Sci. USA* 86:1173–1177), Q-Beta Replicase (Lizardi, P. M. et al., 1988, *BioTechnology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an NPG-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in NPG-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7:244–255; Kozal, M. J. et al. (1996) *Nature Medicine.* 2:753–759). For example, genetic mutations in NPG-1 can be identified in two dimensional arrays containing lightgenerated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NPG-1 gene and detect mutations by comparing the sequence of the sample NPG-1 with the corresponding wild-type (control) sequence. Examples of sequencing reactions include those based on techniques developed by Maxam and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the NPG-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type NPG-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment the control DNA or RNA can be labeled for detection.

In still another embodiment the mismatch cleavage reaction employs one or more proteins that recognize mismatched base pairs in double-stranded DNA (so called "DNA mismatch repair" enzymes) in defined systems for detecting and mapping point mutations in NPG-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an NPG-1 sequence, e.g., a wild-type NPG-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in NPG-1 genes. For example, single strand conformation polymorphism (SSCP) may be used to detect differences in electrophoretic mobility between mutant and wild type nucleic acids (Orita et al. (1989) *Proc Natl. Acad Sci USA* 86:2766, see also Cotton (1993) *Mutat Res* 285:125–144; and Hayashi (1992) *Genet Anal Tech Appl* 9:73–79). Single; stranded DNA fragments of sample and control NPG-1 nucleic acids will be denatured and allowed to renature. The secondary structure of single-stranded nucleic acids varies according to, sequence; the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving an NPG-1 gene.

Furthermore, any cell type or tissue in which NPG-1 is expressed may be utilized in the prognostic assays described herein.

3. Monitoring of Effects During Clinical Trials

Monitoring the influence of agents (e.g., drugs, compounds) on the expression or activity of NPG-1 (e.g., modulation of cellular signal transduction, regulation of gene transcription in a cell involved in development or differentiation regulation of cellular proliferation) can be applied not only in basic drug screening, but also in clinical trials. For example, the effectiveness of an agent determined by a screening assay as described herein to increase NPG-1 gene expression, protein levels, or upregulate NPG-1 activity, can be monitored in clinical trails of subjects exhibiting decreased NPG-1 gene expression protein levels, or downregulated NPG-1 activity. Alternatively, the effectiveness of an agent determined by a screening assay to decrease NPG-1 gene expression protein levels, or downregulate NPG-1 activity, can be monitored in clinical nails of subjects exhibiting increased NPG-1 gene expression, protein levels, or upregulated NPG-1 activity. In such clinical trials, the expression or activity of NPG-1 and, preferably, other genes that have been implicated for example, a proliferative disorder can be used as a "read out" or markers of the phenotype of a particular cell.

For example, and not by way of limitation, genes, including NPG-1, that are modulated in cells by treatment with an agent (e.g., compound, drug or small molecule) which modulates NPG-1 activity (e.g., identified in a screening assay as described herein) can be identified. Thus, to study the effect of agents on proliferative disorders, for example, in a clinical trial, cells can be isolated and RNA prepared and analyzed for the levels of expression of NPG-1 and other genes implicated in the proliferative disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NPG-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimenc, protein, peptide, nucleic acid, small molecule, or other drug candidate identified by the screening assays described herein) comprising the steps of (i) obtaining a pre-administration sample from a subject prior to administration of the agent; (ii) detecting the level of expression of an NPG-1 protein, mRNA, or genomic DNA in the preadministration sample; (iii) obtaining one or more post-administration samples from the subject; (iv) detecting the level of expression or activity of the NPG-1 protein, mRNA, or genomic DNA in the post-administration samples; (v) comparing the level of expression or activity of the NPG-1 protein, mRNA, or genomic DNA in the pre-administration sample with the NPG-1 protein, mRNA, or genomic DNA in the post administration sample or samples; and (vi) altering the administration of the agent to the subject accordingly. For example, increased administration of the agent may be desirable to increase the expression or activity of NPG1 to higher levels than detected, i.e., to increase the effectiveness of the agent. Alternatively, decreased administration of the agent may be desirable to decrease expression or activity of NPG-1 to lower levels than detected, i. e. to decrease the effectiveness of the agent. According to such an embodiment. 'NPG-1 expression or activity may be used as an indicator of the effectiveness of an agent, even in the absence of an observable phenotypic response.

C. Methods of Treatment

The present invention provides for both prophylactic and therapeutic methods of beating a subject at risk of (or susceptible to) a disorder or having a disorder associated with aberrant NPG-1 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the NPG-1 molecules of the present invention or NPG-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant NPG-1 expression or activity, by administering to the subject an agent which modulates NPG-1 expression or at least one NPG. Subjects at risk for a disease which is caused or contributed by aberrant NPG-1 expression or activity can be identified by, for example, any or a combination of diagnostic or prognostic assays as described herein. Administration of a prophylactic agent can occur prior to the manifestation of symptoms characteristic of the NPG-1 aberrancy, such that a disease or disorder is prevented or, alternatively, delayed in its progression. Depending on the type of NPG-1 aberrancy, for example, an NPG-1 agonist or NPG-1 antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating NPG-1 expression or activity for therapeutic purposes. The modulatory method of the invention involves contacting a cell with an agent that modulates one or more of the activities of NPG-1 protein activity associated with the cell. An agent that modulates NPG-1 protein activity can be an agent as described herein, such as a nucleic acid or a protein, a naturally-occurring target molecule of an NPG-1 protein, a peptide, an NPG-1 peptidomimetic, or other small molecule. In one embodiment, the agent stimulates one or more NPG-1 protein activity. Examples of such stimulatory agents include active NPG-1 protein and a nucleic acid molecule encoding NPG-1 that has been introduced into the cell. In another embodiment, the agent inhibits one or more NPG-1 protein activity. Examples of such inhibitory agents include antisense MPG-1 nucleic acid molecules and anti-NPG-1 antibodies. These modulatory methods can be performed in vitro (e.g., by culturing the cell with the agent) or, alternatively, in vivo (e.g., by administering the agent to a subject). As such, the present invention provides methods of beating an individual afflicted with a disease or disorder characterized by aberrant expression or activity of an NPG-1 protein or nucleic acid molecule. In one embodiment, the method involves administering an agent (e.g., an agent identified by a screening assay described herein), or combination of agents that modulates (e.g., upregulates or downregulates) NPG-1 expression or activity. In another embodiment, the method involves administering an NPG-1 protein or nucleic acid molecule as therapy to compensate for reduced or aberrant NPG-1 expression or activity.

Stimulation of NPG-1 activity is desirable in situations in which NPG-1 is abnormally downregulated and/or in which increased NPG-1 activity is likely to have a beneficial effect. Likewise, inhibition of NPG-1 activity is desirable in situations in which NPG-1 is abnormally upregulated and/or in which decreased NPG-1 activity is likely to have a beneficial effect. One example of such a situation is where a subject has a disorder characterized by aberrant development or cellular differentiation. Another example of such a situation is where the subject has a proliferative disease (e.g., prostate cancer).

3. Pharmacogenomics

The NPG-1 molecules of the present invention, as well as agents, or modulators which have a stimulatory or inhibitory effect on NPG-1 activity (e.g., NPG-1 gene expression) as identified by a screening assay described herein can be administered to individuals to treat (prophylactically or therapeutically) disorders (e.g., proliferative or developmental disorders) associated with aberrant NPG-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an NPG-1 molecule or NPG-1 modulator as well as tailoring the dosage and/or therapeutic regimen of treatment with an NPG-1 molecule or NPG-1 modulator.

Pharmacogenomics deals with clinically significant hereditary variations in the response to 'drugs due to altered drug disposition and abnormal action in affected persons. See e.g., Eichelbaum, M. Clin. Exp. Pharmacol. Physiol. (1996) 23(10–11):983–985 and Linder, M. W. Clin. Chem. (1997) 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenenc conditions can occur either as rare genetic defects or as naturally-occurring polymorphisms. For example, glucose-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans. One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60, 000–100, 000 polymorphic or variable sites on the human genome, each of which has two variants). Such a high-resolution genetic map can be compared to a-map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome: In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., an NPG-1 protein or an NPG-1 receptor of the, present invention), all common variants of that gene can be identified in the population and a particular drug response can be associated with one or more genes.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYPZD6-formed metabolite morphine. The other extreme are the so called ulna-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an NPG-1 molecule or NPG-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an NPG-1 molecule or NPG-1 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Experimental Strategy

The LCS method is designed to isolate genes expressed differentially between two cell types or between cells treated in two different ways or for isolation of differences between genomic DNA sequences (FIG. 1). In the first step, both tester DNA and driver DNA are prepared. This is accomplished by digesting the double-stranded cDNA with restriction enzymes of choice, ligating the fragments to amplification tags, e.g., linkers, and carrying out a PCR reaction with linker sequence as primer. The driver DNA is digested with restriction enzymes to remove the linker sequence. In the second step, the tagged/linkered tester DNA is hybridized to an excess of driver DNA (with tags/linkers removed) followed by incubation with mung bean nuclease which digests single-stranded DNA specifically. This leaves only linkered tester-tester homohybrids and unlinkered homo- and heteroduplexes. In the following step, the linkered tester-tester homoduplexes are amplified by PCR with tag/linker sequence as primer to fulfill the first round of enrichment. The amplified PCR products are then used as tester for another round of subtraction. The process of subtractive hybridization, mung bean nuclease digestion, and PCR amplification is carried out three times. Finally, the PCR products of the third round of subtraction are used to prepare a subtraction library by inserting them into a vector.

The following materials and methods were used:

Cell Culture and cDNA Preparation

Human prostate cancer lines LNCaP and PC-3 cells (American Type Culture Collection, Rockville, Md.) were cultured in RPMI-1640 medium with 10% fetal bovine serum, 95% air/5% $CO_2$ at 37° C. Fixed and embedded surgical samples of human prostate cancer and normal prostate tissue were acquired from the Department of Pathology at Beth Israel Deaconess Medical Center, Boston, Mass.

Total RNA was isolated by a guanidinium thiocyanate/phenol method (Xie and Rothblum (1991) *BioTechniques* 11:325–327). Poly(A)$^+$RNA was selected through oligo(dT)$_{25}$-Dynabeads (Dynal Inc., Lake Success, N.Y.). cDNA was synthesized from 2 μg of poly(A)$^+$RNA using a Superscript Choice System (GIBCO, Gaithersburg, Md.) according to the manufacturer's instruction. Oligo(dT)$_{12-18}$ was used to prime the first strand of cDNA synthesis.

Restriction Enzyme Digestion, Linker Ligation, and PCR Amplification

The double-stranded cDNA was digested with Alu I and Rsa I, then ligated with a double-stranded oligodeoxynucleotide linker, which had a blunt end and a 2-base 3' protruding end:

```
ACTCTTGCTTGGACGAGCTCT           (SEQ ID NO:4)

ACTGAGAACGAACCTGCTCGAGA-p       (SEQ ID NO:5)
```

The linker contained an Alu I/Sac I site near the blunt end as indicated. The top strand was designated the amplification primer (AP). The bottom strand was phosphorylated at the 5' end. The linker was prepared by annealing the two strands. An equal mass of each of the two oligodeoxynucleotides was combined. The mixture was heated to 90° C. for 2 minutes, then allowed to cool to room temperature. The ligation was carried out by mixing 1 μg of cut cDNA, 5 μg of linker, 1x ligation buffer (Stratagene, La Jolla, Calif.) and 4 Weiss units of T4 DNA Ligase (Stratagene) in a volume of 10 μl at 8° C., 20 hours. The reaction mixture was electrophoresed through a 2% low-melt agarose gel to remove the unligated linkers. The linker-ligated cDNA fragments in the size range of 0.1–1.0 kb were collected.

Linker-ligated cDNA fragments in agarose were amplified directly by PCR using AP as primer. The reaction (100 μl) contained 10 mM Tris-HCl, pH 8.9, 50 mM KCl, 0.1% Triton X-100, 200 μM dNTPs, 1 μM AP, 2 μM $MgCl_2$, 1 μl of melted agarose, and 5 U of Taq polymerase (Promega), running for 30 cycles (94° C., 1 minute; 55° C., 1 minute; 72° C., 1 minute). The amplified cDNA fragments were purified using a Gene-Clean kit (Bio101, Vista, Calif.) and were used as the initial material for subtractive hybridization.

Subtractive Hybridization

Twenty μg of PCR-amplified driver DNA were digested with AluI (50 units), 37° C., 2 hours, followed by Sac1 (50 units), 1 hour to cleave the linker so that driver DNA could not be amplified later. After digestion, the products were purified using Gene-Clean (BIO 101, La Jolla, Calif.).

The digested driver DNA (2.5 μg) and nondigested tester DNA (0.1 μg) were mixed, vacuum-dried and redissolved in 4 μl of a buffer containing 15 mM N-(2-hydroxy ethyl) piperazine-N'-(3-propane sulfonic acid) (EPPS), pH 8.0/1.5 mM EDTA, overlaid with mineral oil, and denatured by heating for 5 minutes at 100° C. One μl of 5 M NaCl was added, and the DNA was hybridized for 20 hours at 67° C. After hybridization, 20 μl of PH-shift buffer A (1 mM $ZnCl_2$, 10 mM Na acetate, pH 5.0) was added and the solution was divided into 5 aliquots. The aliquots were incubated with 0, 0.85, 1.75, 3.5, or 7 units of mung bean nuclease (Promega), respectively, at 37° C. for 30 minutes. To each sample 80 μl of pH-shift buffer B (10 mM Tris-HCl, pH 8.9, 50 mM KCl, and 0.1% Triton X-100) were added and the samples were heated at 95° C. for 5 minutes to inactivate the mung bean nuclease. Then, 20 μl of enzyme solution (10 mM Tris-HCl, pH 8.9, 50 mM KCl, and 0.1% Triton X-100, 1 mM dNTPs, 5 μM AP, 10 mM $MgCl_2$ and 5 units of Taq polymerase (Promega) was added. The PCR reaction was run under the same conditions as above. Each sample was electrophoresed on a 2% agarose gel. The sample with the most abundant products of 0.1–1.0 kb was selected as tester for another round of subtraction. The above process was repeated twice with 2.5 μg of driver DNA and 0.025 μg of tester DNA. To test for enrichment of target sequences, PCR products derived from subtraction cycles 0–3 were electrophoresed on 4% NuSieve agarose (FMC, Rockland, Me.), transferred to GeneScreen Plus membrane Dupont/NEN, Boston, Mass.) and probed with the random-labeled PCR products (with linkers removed) of the third round of subtraction.

Construction of Subtractive Library and Clonal Analysis

After three rounds of subtraction, the PCR-amplified products were purified (GeneClean, Bio101, La Jolla Calif.), digested with SacI, inserted into dephosphorylated pGEM-7Zf (+) vector (Promega) at the SacI site and transformed into competent *E. coli* JM 109 cells. Two subtractive libraries were prepared in this way: LNCaP (tester)/PC3 (driver)= "L-P", and PC-3 (tester)/LNCaP (driver)="P-L".

Forty eight white colonies from each library were picked randomly and inoculated into LB +Amp medium in individual wells of a 96-well plate. Two replica DNA dot-blots were prepared on GeneScreen Plus filters using 25 μl of bacterial cells per well. The replica dot-blots were processed according to Brown and Knudson ((1991) *BioTechniques* 10:719–722) and probed with random-labeled driver DNAs from LNCaP and PC-3, respectively.

Candidate positive colonies were boiled for 5 minutes in 20 μl $H_2O$ and centrifuged. DNA in the supernatant was amplified by PCR using universal vector primer T7 and SP6 for 20 cycles of 94° C. for 1 minute; 55° C. for 1 minute; and 72° C. for 1 minute. The PCR products were electrophoresed on a 2% agarose gel. The desired bands were excised and purified (Gene-Clean). The products were subjected to direct DNA sequencing (Brown and Knudson (1991) *BioTechniques* 10:719–722), and were employed as probes in Northern blot analyses.

Cloning and Analysis of Differentially Expressed Genes Between the Human Prostate Cancer Cell Lines LNCaP and PC-3

The strategy outlined above was used to begin to clone and identify the genes expressed differentially between the human prostate cancer cell lines LNCaP and PC-3, which have different tumorigenic and metastatic potentials. After three cycles of subtraction, the PCR products were cleaved with SadI, inserted into pGEM-7Zf (+) and transformed into *E. coli* JM 109 cells. The PCR-amplified DNA derived from subtraction cycles 0–3 was electrophoretically analyzed. 10 µl of PCR reaction mixture were electrophoresed on a 4% NuSieve agarose gel. The original unsubtracted DNAs from LNCaP and PC-3 moved as a smear between 0.1–1.0 Kb. As subtraction rounds were performed, distinct bands were seen. The intensity and resolution of these bands increased progressively with successive subtraction. When labeled PCR products of the third round of subtraction were electrophoresed on a 6% sequencing gel, 50–60 bands could be seen. DNA of the agarose gel was transferred to Gene Screen Plus membrane, and probed with the labeled PCR products of the third round of subtraction L-P, 3 or P-L, 3. The results indicated strong enrichment of differentially expressed sequences.

After three rounds of subtraction, the PCR-amplified products were inserted into pGEM-7Zf(+) and transformed into *E. coli* JM 109 cells. Forty-eight white colonies were randomly picked from each of the libraries and grown in LB medium in individual wells of a 96well plate. Two replica DNA dot-blots were prepared and probed with the labeled driver DNAs from LNCaP and PC-3, respectively. A comparison of the hybridization intensity of a clone in two replica membranes revealed the relative abundance of the transcript in the two cell types. Over two-thirds of the selected clones demonstrated significant differences in abundance. Clones were tested further by Northern blot. Briefly, 5 pg of total RNA from LNCaP or PC-3 cells was electrophoresed in a 1% agarose/formaldehyde gel, transferred to a GeneScreen Plus membrane and probed with the $^{32}$P random labeled PCR products.

The clones were then sequenced by direct DNA sequencing. Specifically, the amplified DNA fragments were isolated by agarose gel electrophoresis and purified using a Gene-Clean kit. The DNA was sequenced with the same primer used for amplification by the direct sequencing procedure from the "Sequenase" protocol (United States Biochemical Corp., Cleveland, Ohio) as modified by Winship ((1989) *Nucleic Acids Res.* 17:1266).

From 78 colonies, 15 distinct clones were identified which correspond to mRNAs expressed differentially between LNCaP and PC-3 cell lines. The extent of differential expression ranged from several fold to greater than 100 fold. Using the method of the invention, five novel genes were identified as well as-other known genes which are or may be involved in signal transduction, tumor growth, tumor invasion and metastasis. A Northern blot exemplifying differential expression of two genes was performed. Total RNA from lNCaP and PC-3 cells was electrophoresed and probed with radiolabeled cDNA of two differentially expressed clones isolated by LCS. DNA sequence analyses demonstrated that the LNCaP specific gene is prostate specific antigen (PSA) which is known to be expressed in LNCaP but not in PC-3 (Winship (1989) *Nucleic Acids Res.* 17:1266). The PC-3 specific gene was found to be vimentin, the differential expression of which has not been reported previously in these prostate cancer cells.

Differential expression of candidate positives was confirmed by northern analyses of LNCaP and PC-3 RNA using isolated clones as probes. Laser scanning densitometry of the autoradiograms was used to quantify steady state transcript levels. The degree of differential expression of thirteen confirmed positives was quantified by laser scanning densitometry and was found to range from several-fold to greater than 100-fold (Table 1).

The partial DNA sequences of the isolated cDNAs were determined and homology searches in GenBank were performed using BLAST (Table 1). Of the thirteen genes identified thus far, ten are known and three are novel (Table 1). As we reported previously, prostate specific antigen (PSA) was expressed in LNCaP but not in PC3, whereas vimentin was expressed in PC-3 but not in LNCaP. The complete coding sequence of NPG-1 is shown in FIG. 2.

Among the other known genes, prostate specific antigen and the human selenium binding protein hSP56 were expressed preferentially by LNCaP, whereas vimentin, annexin II, calcyclin, $p^{INK4}$ (MTS-1), uridine phosphorylase, keratin K7, ferritin (light chain) and aenolase were expressed preferentially by PC-3. Interestingly, three novel genes were identified. These have been designated: novel prostate gene 1, 2 and 3 (NPG-1, NPG-2, NPG-3). Both NPG-1 and NPG-2 were expressed only by LNCaP. In contrast, NPG-3 expression was much higher in PC-3.

TABLE 1

Genes Expressed Differentially in Human Prostate Cancer Cell Lines LNCaP and PC-3: Detected by Linker Capture Subtraction

| | DNA Sequence Clone Identification | Transcript Size, kb | Insert Size, bp | Expression Ratio LNCaP/PC-3* |
|---|---|---|---|---|
| 1 | prostate specific antigen+ | 1.8 | 347 | >100 |
| 2 | vimentin+ | 2.0 | 79 | >0.01 |
| 3 | annexin II | 1.8 | 187 | >0.01 |
| 4 | calcyclin | 0.6 | 205 | >0.01 |
| 5 | p15$^{INK4}$(MTS-1) | 0.8 | 180 | >0.01 |
| 6 | hSP56 | 1.9 | 230 | >100 |
| 7 | uridine/phosphorylase | 2.0, 1.6 | 216 | >0.01 |
| 8 | keratin K7 | 2.3 | 146 | >0.07 |
| 9 | ferrintin (light chain) | 1.5 | 189 | >0.25 |
| 10 | a-enolase | 2.0 | 148 | >0.33 |
| 11 | novel prostate gene 1 (NPG-1) | 2.0 | 400 | >100 |
| 12 | novel prostate gene 2 (NPG-2) | 0.8 | 197 | >100 |
| 13 | novel prostate gene 3 (NPG-3) | 1.9 | 223 | >0.07 |

*Integrated absorbance units (I.A.U.) were generated by quantitative two dimensional laser densitometric scanning of autoradiograms prepared from northern blots. The expression ratio = LNCaP.
I.A.U./PC-3 I.A.U. ">100" signifies no transcript detected in PC-3.
"<0.01" signifies no transcript detected in LNCaP.
+Reported previously (Yang, M. et al. (1996) Analytical Biochem., 237: 109–114).

In situ Hybridization for NPG-1 Expression

One µg of the recombinant pGEM-7Zf(+) (Promega) containing the 400 base pair insert of NPG-1 was used as template to generate antisense and sense transcripts. Plasmids were linearized with the appropriate enzymes and transcribed using SP6 and T7 RNA polymerase for 1 hour at 37° C. in 1xtranscription buffer (Promega, Madison, Wis.)

10 mM dithiothreitol (DTT), 40 U of RNAse inhibitor, mM I each of ATP, CTP and GTP, as well as 1 mM of a mixture of cold UTP and digoxigenin-UTP (6.5 and 3.5 mM respectively), to generate sense and antisense RNAs. The presence of a single band on 1% agarose gel in which the precipitated probe was run confirmed prior to use of the riboprobe.

In situ hybridization with digoxigenin labeled NPG-1 was performed on an automated instrument (Gen II, Ventana Medical Systems, Tucson, Ariz.) in which duration and temperature of all the steps are standardized. Five µm formalin-fixed paraffin-embedded prostate sections were dewaxed, rehydrated, digested with proteinase K (50 µg/ml) in 1 M Tris-EDTA buffer (pH 8) for 8 minutes at 37° C. Hybridization with riboprobes (sense and antisense) was performed at 42° C. for 1 hour applying 10 µM of digoxigenin-labeled riboprobe in 100 µl of hybridization buffer (50% deionized formamide, 2×SSC, 10% dextra sulphate, 1% SDS, 250 µg/ml denatured herring sperm DNA) per section, under a liquid coverslip. The ideal hybridization and stringency conditions are partially based on sequence but usually have to be determined empirically because of different methods of tissue preservation, fixation, and abundance of target. Thus, in order to establish the appropriate conditions for NPG-1, we progressively increased stringency washes after the initial low stringency 42° C. hybridization. Hybridization was followed by four washes of decreasing amounts of SSC up to 0.1×SSC until there was complete loss of signal for the sense probe. Alkaline phosphatase-conjugated anti-digoxigenin antibody (1:500) was applied for 28 minutes at 37° C. Detection was accomplished with nitro blue tetrazolium/5-bromo 4-chloro 3indolyl phosphate (NBT/BCIP) as a substrate for 8 minutes. Hybridization controls were performed pretreating tissue sections with RNAse A for 1 hour at 37° C. Expression of NPG-1, when present, was found throughout the tumor. Sections were evaluated for intensity of staining, which was scored as 0, $1^+$, $2^+$ or $3^+$. The joint variation of Gleason grade with NPG-1 expression was measured through the calculation of the correlation coefficient (r) using the Fisher transformation.

NPG-1 was found to be expressed in 23 of 28 tumors examined. NPG-1 was highly expressed in the cancerous portion of the prostate. However, in the adjacent normal portion of the gland, NPG-1 expression was restricted entirely to the basal epithelial cell layer.

The degrees of NPG-1 expression in the cancerous portion correlated with an aggressive histopathology. The tumor samples had previously and independently been graded according to the Gleason criteria (described in, for example, Epstein, J. I. Grading of prostatic adenocarcinoma. In: Prostate Biopsy Interpretation. 2nd edition, pp.65–85, Lippincott-Ravin, Philadelphia, 1995). NPG-1 expression was quantified according to a scale of 0, $1^+$, $2^+$ or $3^+$ established previously for gene expression demonstrated by in situ hybridization (described in, for example, Tan, P. et al. (1997) *Cancer Res.*, 57:1259–1263). Statistical analysis of these results revealed a positive correlation between the Gleason grade and the degree of NPG-1 expression (correlation coefficient r=0.463) that was statistically significant p=0.02).

NPG-1 expression was found in the large majority of primary tumors examine; and there was a significant correlation between the degree of expression and the Gleason grade of the tumor. This demonstrates that NPG-1 is useful as a diagnostic and/or prognostic marker. Secondly, whereas NPG-1 expression was strong in the cancerous portion of the gland, within the normal tissue it was restricted to cells in the basal epithelial layer. It has been proposed that this layer contains the relatively undifferentiated "prostatic stem cell". This pattern of expression demonstrates that at least some prostate cancers may arise from such immature cells.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method for detecting the presence of a nucleic acid molecule encoding NPG-1 in a sample comprising:
   a) contacting the sample with a nucleic acid probe or primer which hybridizes under stringent conditions to a nucleic acid molecule of SEQ ID NO:1; and
   b) determining whether the nucleic acid probe or primer binds to a nucleic acid molecule in the sample to thereby detect the presence of a nucleic acid molecule encoding NPG-1 in the sample.

2. The method of claim 1, wherein the sample comprises mRNA molecules and is contacted with a nucleic acid probe.

3. A kit comprising a compound which hybridizes under stringent conditions to a nucleic acid molecule of SEQ ID NO:1 and instructions for use.

4. The method of claim 1, wherein the sample is obtained from a subject having prostate cancer.

5. A method of determining the stage of prostate cancer development in a subject having prostate cancer, comprising:
   contacting a sample obtained from the subject with a nucleic acid probe or primer which hybridizes under stringent conditions to a nucleic acid molecule encoding NPG-1; and
   determining whether the nucleic acid probe or primer binds to a nucleic acid molecule in the sample to thereby detect the presence of a nucleic acid molecule encoding NPG-1 in the sample.

6. The method of claim 5, wherein the nucleic acid probe hybridizes under stringent conditions to a nucleic acid of SEQ ID NO:1.

7. The method of claim 5, wherein the presence of NPG-1 in the sample is indicative of the subject having an androgen-dependent prostate cancer.

8. The method of claim 5, wherein the absence of NPG-1 in the sample is indicative of the subject having an androgen-insensitive prostate cancer.

9. A method of determining malignant transformation in a subject having prostate cancer, comprising:
   contacting a first sample obtained from the subject with a nucleic acid probe or primer which hybridizes under stringent conditions to a nucleic acid molecule encoding NPG-1;

determining the level of NPG-1 expression in the first sample;

contacting a second sample obtained from the subject with a nucleic acid probe or primer which hybridizes under stringent conditions to a nucleic acid molecule encoding NPG-1;

determining the level of NPG-1 expression in the second sample;

comparing the level of NPG-1 expression in the first sample with the level of NPG-1 expression in the second sample, to thereby determine if there has been transformation of the prostate cancer.

10. The method of claim 9, wherein the nucleic acid probe hybridizes under stringent conditions to a nucleic acid of SEQ ID NO:1.

11. The method of claim 9, wherein a decrease in NPG-1 levels is indicative malignant transformation of the prostate cancer.

12. The method of claim 9, wherein an increase in NPG-1 levels or maintenance of NPG-1 levels between the first and second sample indicates that the prostate cancer is not undergoing malignant transformation.

13. The method of claim 9, wherein the first sample is obtained from the subject prior to administration of a treatment to the subject.

14. The method of claim 13, wherein the second sample is obtained from the subject after administration of a treatment to the subject.

* * * * *